US006571294B2

(12) United States Patent
Simmon et al.

(10) Patent No.: US 6,571,294 B2
(45) Date of Patent: *May 27, 2003

(54) BAR-CODE-DRIVEN DATA ACQUISITION AND MANAGEMENT SYSTEM

(75) Inventors: Arnulf Simmon, Bozeman, MT (US); Brett Donahue, Bozeman, MT (US)

(73) Assignee: Metrologic Instruments, Inc., Blackwood, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/821,731

(22) Filed: Mar. 29, 2001

(65) Prior Publication Data

US 2002/0040406 A1 Apr. 4, 2002

Related U.S. Application Data

(63) Continuation of application No. 09/241,214, filed on Feb. 1, 1999, now Pat. No. 6,389,477, which is a continuation of application No. 08/196,452, filed on Feb. 14, 1994, now Pat. No. 5,867,688.

(51) Int. Cl.[7] .............................................. G06F 13/00

(52) U.S. Cl. ...................................................... 709/234

(58) Field of Search ................................ 709/200, 208, 709/230, 231, 232, 233, 234–236, 238; 345/156, 173, 168, 169

(56) References Cited

U.S. PATENT DOCUMENTS

| 3,685,723 | A | 8/1972 | Berler |
| 3,826,900 | A | 7/1974 | Moellering |
| 4,121,574 | A | 10/1978 | Lester |
| 4,279,021 | A | 7/1981 | See et al. |

(List continued on next page.)

FOREIGN PATENT DOCUMENTS

GB 2362059 A 11/2001

OTHER PUBLICATIONS

Terminal Support Unit (TSU) by CliniCom Inc., Boulder CO, 2000.

(List continued on next page.)

*Primary Examiner*—Robert B. Harrell
(74) *Attorney, Agent, or Firm*—Thomas J. Perkowski, Esq., P.C.

(57) ABSTRACT

A bar-code-driven data acquisition and management system includes at least two input computers, operably coupled via a communication link, each coupled to a respective local database of data records. The system includes at least two portable computing devices, each operably coupled to one of the two input computers via a wireless communication channel for accessing the data records of the local databases of the at least two input computers. Each portable computing device comprises a CPU, memory, and a touch sensitive display device that cooperate to display multiple virtual regions (which comprise on a data I/O screen and sense location of contact by a user in these virtual regions to thereby provide for user input. These multiple virtual regions preferably include one of a virtual keypad for entering symbols associated with keys of the keypad, at least one scroll bar, at least one rolling key, multiple icons, a menu screen and a graphing screen. In addition, each portable computer has an integrated bar code reader for data entry. The information acquired and maintained by the system may include product information, information identifying a medical patient. or information related a medical patient (such as personal information gathered upon admittance for care, information related to past medical history of the medical patient, and information related to vital statistics of the medical patient). In addition, each portable device may include a message notification mechanism that notifies the user of receipt of a message from one of the input computers over the respective wireless communication channels.

25 Claims, 17 Drawing Sheets

U.S. PATENT DOCUMENTS

| | | | |
|---|---|---|---|
| 4,143,417 | A | 3/1979 | Wald et al. |
| 4,210,802 | A | 7/1980 | Sakai |
| 4,224,615 | A | 9/1980 | Penz |
| 4,251,798 | A | 2/1981 | Swartz et al. |
| 4,408,120 | A | 10/1983 | Hara et al. |
| 4,409,470 | A | 10/1983 | Shepard et al. |
| 4,456,793 | A | 6/1984 | Baker et al. |
| 4,471,165 | A | 9/1984 | DeFino et al. |
| 4,486,624 | A | 12/1984 | Puhl et al. |
| 4,491,725 | A | 1/1985 | Pritchard |
| 4,503,288 | A | 3/1985 | Kessler |
| 4,569,421 | A | 2/1986 | Sandstedt |
| 4,570,057 | A | 2/1986 | Chadima, Jr. et al. |
| 4,575,625 | A | 3/1986 | Knowles |
| 4,578,571 | A | 3/1986 | Williams |
| 4,593,155 | A | 6/1986 | Hawkins |
| 4,621,189 | A | 11/1986 | Kumar et al. |
| 4,625,276 | A | 11/1986 | Benton et al. |
| 4,763,356 | A | 8/1988 | Day, Jr. et al. |
| 4,773,032 | A | 9/1988 | Uehara et al. |
| 4,835,372 | A | 5/1989 | Gombrich et al. |
| 4,850,009 | A | 7/1989 | Zook et al. |
| 4,916,441 | A | 4/1990 | Gombrich |
| 5,031,119 | A | 7/1991 | Dulaney |
| 5,038,284 | A | 8/1991 | Kramer |
| 5,056,059 | A | 10/1991 | Tivig et al. |
| 5,067,103 | A | 11/1991 | Lapeyre |
| 5,133,076 | A | 7/1992 | Hawkins et al. |
| 5,227,614 | A | 7/1993 | Danielson et al. |
| 5,386,219 | A | 1/1995 | Greanias et al. |
| 5,428,417 | A | 6/1995 | Lichtenstein |
| 2001/0029534 | A1 | 10/2001 | Spinks et al. |
| 2002/0069269 | A1 | 6/2002 | Simpson |

OTHER PUBLICATIONS

The Bedside Story by CliniCom, Inc., Boulder CO, 2000.
Cliniview with Touchscreen by CliniCom Inc., Boulder CO, 2000.
Bedside Data System Aids Pharmacy by Karen Gammon, et. al., Boulder Memorial Hospital, Boulder CO, 2000, p. 35–37.
Bedside Matters. by CliniCom Incorporated, Boulder CO, 2000.
Pen Operating Systems by Bruce Brown, PC Magazine, 1993, p. 172.
Keyboard–Based Organizers by Jeff Greenberg, PC Magazine, 1993, p. 166–167.
Mainstream Pen–Based Portables by Don Crabb, PC Magazine, 1993, p. 144–145.
Vertical–Market Pen Tablets by Don Crabb, PC Magazine, 1993, p. 157.
Pen Pals by Christopher Barr and Michael Neubarth, PC Magazine, 1993.
Cliniview by CliniCom Inc., Boulder CO, 1989.
Point of Care Terminal by CliniCom Inc., Boulder CO, 1988.
Bedside Terminals: CliniCom by Shirley Hughes, M.D. Computing, vol. 5, No. 1, 1988.
Cost Benefit Analysis of the Clinicare Handheld Terminal System by Shirley Hughes, et. al., CliniCom Incorporated, 1987.
Qualitative & Quantitative Benefits of the Clinicare Bedside System by CliniCom, by Ray Uhlorn, et. al., CliniCom, Inc., Boulder CO, 1987.
Patient Information at the Point–of–Care by CliniCom, Inc., Boulder CO, 1987.
Travenol Laboratories: A Leader in HIBC by Peter C. Doyle, Bar Code News, 1986.
Bar Code Finds Identity as User Input Alternative by Ron Schneiderman, News Views, 1985.
Databar by Databar Corporation, 1984.
Bar Coding For Medical Device Labeling by Richard Fard, MG & DI, 1983.
A Uniform Labeling System for Blood Services by Richard C. Hubbell, et. al., Medical Instrumentation, vol. 15, No. 1, 1981.
An Integrated Hospital Computer System by B.A.W. Stobart, et. al., Systems Technology, No. 30, 1978.
CliniCom (TM) Product Information Sheet entitled Terminal Support Unit (TSU) by CliniCom Inc., Boulder CO, 1998, 1 page.
CliniCom (TM) Newsletter entitled The Bedside Story by CliniCom, Inc., Boulder CO, 1998, pp. 1–6.
CliniCom (TM Product Information Sheet) entitled Cliniview with Touchscreen by CliniCom Inc., Boulder CO, 1989, 1 page.
Computers in Healthcare article entitled Bedside Data System AIDS Pharmacy by Karen Gammon, et. al., Boulder Memorial Hospital, Boulder CO, 1988, p. 35–37.
CliniCom (TM) Product Brochure entitled Bedside Matters. by CliniCom Incorporated, Boulder CO, 1989, 7 pages.
PC Magazine article entitled Keyboard–Based Organizers by Jeff Greenberg, PC Magazine, 1993, p. 166–167.
PC Magazine article entitled Mainstream Pen–Based Portables by Don Crabb, PC Magazine, 1993, p. 144–145.
PC Magazine article entitled Pen Pals by Christopher Barr and Michael Neubarth, PC Magazine, 1993, 16 pages.
CliniCom (TM) Product Information Sheet entitled Point of Care Terminal by CliniCom Inc., Boulder CO, 1988, 1 page.
CliniCom (TM) Product Information Sheet entitled Point of Care Terminal by CliniCom Inc., Boulder CO, 1988, 1 page.
M.D. Computing article entitled Bedside Terminals: CliniCom by Shirley Hughes, M.D. Computing, vol. 5, No. 1, 1988, 7 pages.
CliniCom (TM) presentation entitled Cost Benefit Analysis of the Clinicare Handheld Terminal System by Shirley Hughes, et. al., CliniCom Incorporated, 1987, 22 pages.
CliniCom (TM) paper entitled Qualitative & Quantitative Benefits of the Clinicare Bedside System by Ray Uhlorn, et. al., CliniCom, Inc., Boulder CO, 1987, 12 pages.
CliniCom (TM) Product Information Sheet entitled Patient Information at the Point–of–Care by CliniCom, Inc., Boulder CO, 1987, 6 pages.
Travenol Laboratories: A Leader in HIBC by Peter C. Doyle, Bar Code News, 1986, 5 pages.
Systems of Software article Bar Code Finds Identity as User Input Alternative by Ron Schneiderman, News Views, 1985, 3 pages.
Databar (TM) Product Brochure, by Databar Corporation, 1984, 11 pages.
Bar Coding for Medical Device Labeling by Richard Fard, MG & DI, 1983, 5 pages.
A Uniform Labeling System for Blood Services by Richard C. Hubbell, et. al., Medical Instrumentation, vol. 15, No. 1, 1981, 3 pages.
An Integrated Hospital Computer System by B.A.W. Stobart, et. al., Systems Technology, No. 30, 1978, 6 pages.

BAR-CODE-DRIVEN DATA ACQUISITION AND MANAGEMENT SYSTEM

RELATED CASES

This Application is a Continuation of U.S. application Ser. No. 09/241,214 filed Feb. 1, 1999, now U.S. Pat. No. 6,389,477; which is a Continuation of U.S. application Ser. No. 08/196,452 filed Feb. 14, 1994, now U.S. Pat. No. 5,867,688. Each said patent application is assigned to and commonly owned by Metrologic Instruments, Inc. of Blackwood, N.J., and is incorporated herein by reference in its entirety.

BACKGROUND OF THE INVENTION

1. Field of the Invention

The present invention relates in general to a system for data acquisition and retrieval through the use of a user interface remotely located from the control system.

2. Description of the Related Art

Today, most commercial businesses require field employees, such as at points of sale, to fill out paper forms with data sets concerning individual customers or products sold/manufactured. These reports are then collected, compiled and assimilated at a central location and filed for future access. Most modern businesses require this information to be continuously updated and that the field personnel be afforded quick access thereto in order to reduce business costs, improve efficiency, increase accuracy, and the like. Heretofore, data sets concerning matters, such as customer or product information, have been primarily compiled through paper forms completed by field personnel and later possibly entered into some form of central database.

In the healthcare field, hospitals utilize a significant amount of data retrieval and acquisition, with respect to patient information. All data sets containing patient information (data field), such as patient name (a data set, header), date of birth, place of business, address, phone numbers, language, billing account number, social security number, drivers license number, and the like were written on paper forms and maintained in a paper file, and optionally entered by the hospital staff into a common database. Thereafter, the patient information was supplemented with information pertaining to their health condition, such as vital signs, fluid intake, fluid output and the like, which were written on different paper forms by a nurse and later keyed into this common database. Similarly, when patients undergo testing, the test results were manually keyed into the common database and/or written on forms stored in the patient's paper file.

An alternative example lies in the insurance industry in which field claims adjustors travel to the site of an insurance claim and evaluate the damaged property. These adjustors fill out multiple forms identifying the damage and the insured person's general information. For instance, in an automotive accident the claims adjustor must describe each problem with the insured car, such as dents, scratches, and the like. These forms are later processed manually or keyed into a common database, after which, the claimant ultimately is paid.

A substantial amount of data acquisition and retrieval is also utilized in factory environments. During the course of manufacturing various products, floor workers and quality review must complete multiple forms concerning a given production unit.

However, every business requiring significant amounts of data acquisition and retrieval in its day-to-day business encounter similar problems. First and foremost, a significant amount of the field operative's time is required in filling out the corresponding paperwork, in which the potential for user error exists. Also, in systems using paper forms, the information must be ultimately transferred to an electronic database, which provides a second opportunity for user error. Clearly, it would be advantageous to reduce the number of user entries, thereby reducing the likelihood of error.

Further, in many markets, field personnel at one location typically require information quickly from another field location. For instance, in a hospital environment, a doctor within the general ward may require immediate information concerning a patient from the radiology department. However, the process under which the information is written down and carried between departments is very slow. Similarly, doctors and nurses require immediate and accurate knowledge of specific procedures to be followed with regard to particular patients. Past systems for maintaining individual patient procedures have proven ineffective.

Moreover, one office within a business will typically require information from another office which must be hand carried or which is unavailable after the closing hours of the second office. For instance, hospitals require lab testing results be hand-carried to doctors who may be waiting for such results during the course of surgery. Also, typically doctors require clinical data after the clinics have closed.

The need remains in this field for an improved data acquisition and retrieval system to address the problems and drawbacks heretofore experienced. The primary objective of this invention is to meet this need.

SUMMARY OF THE INVENTION

It is an object of the present invention to provide a data acquisition and retrieval system which allows users immediate real time access to all existing customer/product information.

It is an object of the present invention to provide a data acquisition and retrieval system which affords users access to wireless remote data terminals.

It is an object of the present invention to minimize the data retrieval time by reducing the necessary information transmitted between handheld units and the corresponding communications server.

It is another object of the present invention to minimize the data necessary for transmission by synchronizing operation within each handheld unit and a corresponding communications server, such synchronization including the minimization of header information for each transmission and the transmission of a command case code used directly by the command server to access a designated database.

It is another object of the present invention to provide a user interface which minimizes user error.

It is another object of the present invention to provide a user interface which utilizes an event driven architecture to allow data entry through a touch pad.

It is another object of the present invention to provide a user interface which is easily operated by using a touch pad which presents a scroll bar, rolling keys and icons for data entry.

It is another object of the present invention to provide a user interface which allows for the scanning of bar codes to identify particular customers or products.

These and further objects will become more apparent from the drawings and detailed description hereafter.

BRIEF DESCRIPTION OF THE DRAWINGS

The objects and features of the invention noted above are explained in more detail with reference to the drawings, in which like reference numerals denote like elements, and in which.

DETAILED DESCRIPTION OF THE INVENTION

Overview

Figure 1:
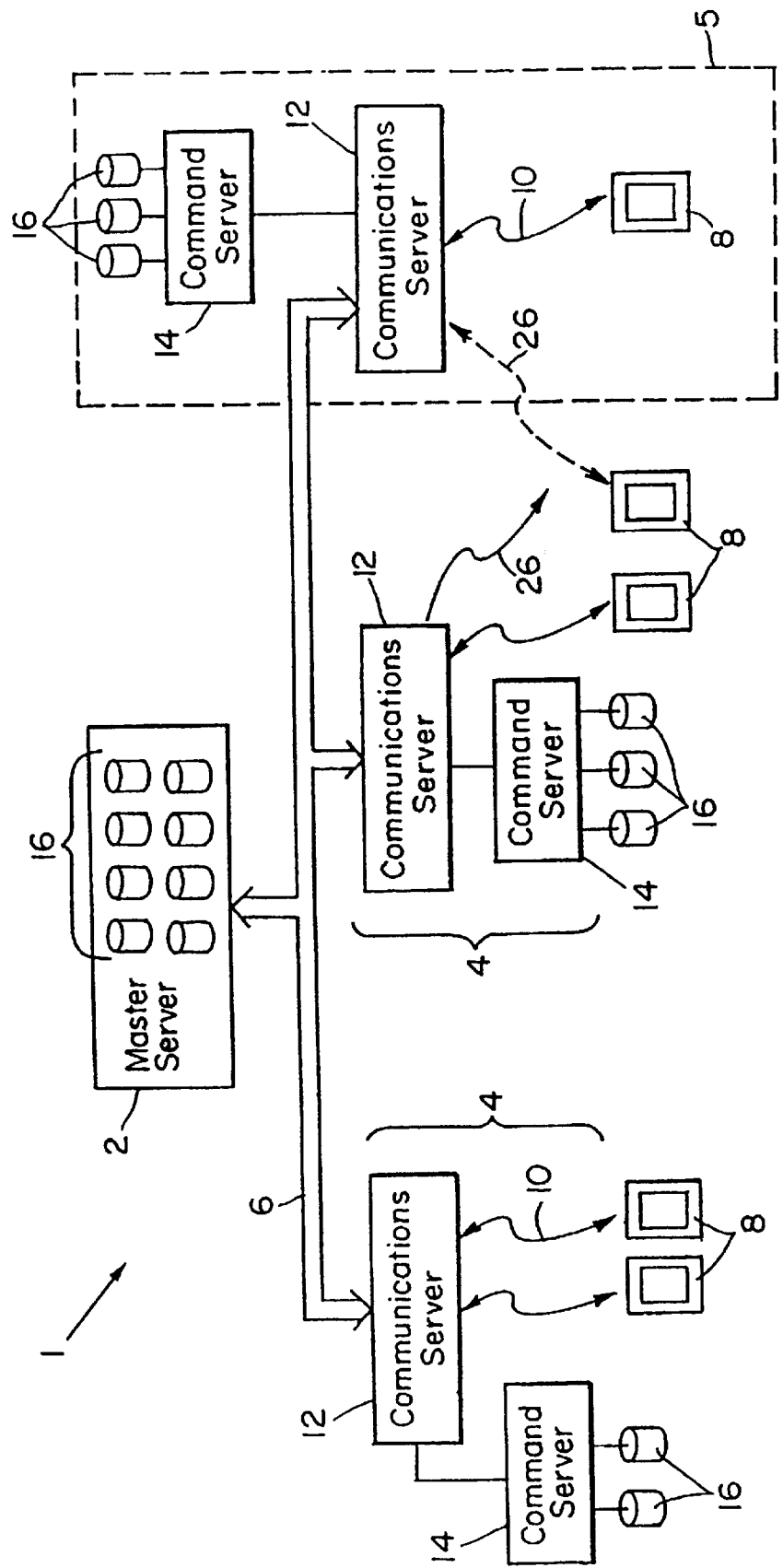
FIG. 1 is a block diagram of an overview of a data acquisition and retrieval system according to the present invention.

FIG. 1 illustrates a data retrieval/acquisition system according to the present invention generally illustrated by the reference numeral 1. The instant system 1 includes a master server 2 which communicates with multiple remote input units 4 through a communications bus 6. Each input unit 4 includes a communications server 12 directly connected to a command server 14 and data bases 16. Each remote communications server 12 interactively communicates with one or more handheld user interfaces 8 while located within a predefined region 5 proximate thereto. This interactive communication is conducted through a wireless dedicated communication channel, such as upon an infrared carrier signal.

The communications server 12 controls all interaction between the handheld interfaces 8, the command servers 14, and the communications bus 6. The command servers 14 control direct access to the databases 16. The command servers 14 may implement any conventionally known IO management system, such as Pro-Tree (version 2.0), SQL or Paradox. The communications server 12 communicates with each handheld interface 8 through a unique communications protocol (hereafter referred to as the Handheld-Server Protocol). The communications server 12 communicates with the command servers 14 through a unique protocol (hereafter referred to as the Message List Protocol).

As explained below, the communications server 12 synchronizes its operations with those of the handheld interfaces 8 to minimize the excess data necessary for each transmission therebetween. The communications server 12 and interface 8 also utilize shorthand code values to identify constantly transmitted information, such as commands, user IDs, database IDs, and the like. By synchronizing operation of the handheld interface 8 and the corresponding communications server 12, the instant system is able to avoid the need to transmit the user ID, time, date, authorization code, and the like during every transmission.

During operation, the user enters data at the handheld interface 8, the data is transmitted to the communications server 12 and stored internally within the database 16. Data may also be entered directly into the communications server 12. Similarly, the user may request data previously submitted, in which case the communications server 12 accesses the corresponding database 16, through the command server 14, and transmits the necessary desired information to the requesting handheld interface 8. Throughout operation, a backup copy may be maintained within the master server 2 for every remote database 16. Additionally, the user may request, via the handheld interface 8, data stored within a remote input unit 4 other than the data in the databases directly connected to the receiving communications server 12. In such a circumstance, the corresponding communications server 12 would accept the request from the handheld interface 8, determine that the desired information is stored within a remote database and request such information through the communications bus 6 from the communications server 12 containing the corresponding database. Thus, the communications bus 6 also allows data to be transmitted between communications servers 12 and between handheld interfaces 8 (such as when one doctor is requesting information from another doctor).

By way of example only, the instant acquisition/retrieval system 1 may be utilized within a healthcare facility wherein doctors, nurses, and staff utilize the handheld interfaces 8 to record and obtain patient information. These persons may be assigned different privileges which would allow varying levels of access to data. In this environment, each communications server may be located within a different ward or testing laboratory. Thus, a doctor in a general ward may need to send a message to, or obtain information from, a doctor or nurse in radiology. To do so, the doctor would transmit a request through the handheld interface 8, with the request being received and decoded in the general ward's communications server 12. The source/receiving communications server determines the appropriate destination communications server that corresponds to the destination handheld interface, into which the destination doctor or nurse has signed on. The desired message is transmitted to the radiology server, and to the corresponding handheld interface which queries the user through audio, video, or vibrating means. In a similar manner, the user within radiology may transmit a response through the corresponding radiology and general ward communications servers 12 to the requesting doctor's handheld interface 8. Also, lab data may be quickly transmitted to a surgeon during an operation.

The instant acquisition/retrieval system 1 also allows doctors, nurses, and staff members immediate access to clinical data, even after clinic hours are closed. To do so, the user merely enters a request through his/her handheld interface 8, which is transmitted through the corresponding communications server 12 to the clinical communications server 12. The necessary clinical data is obtained from the clinical database and returned along the communications bus 6. By way of example, the data acquisition/retrieval system 1 of the healthcare facility may be connected to similar systems via an ethernet connected between the master servers 2.

The handheld interfaces 8 are used to enter all patient information such as personal information upon admittance, past medical histories, vital statistics throughout their stay in the hospital, and the like. For instance, these vital statistics may include systolic, diastolic, pulse, temperature, and respiratory information. Similarly, the handheld interface 8 may be used to enter information concerning the patient's fluid intake and output.

As will be explained below, the instant data acquisition/retrieval system 1, also allows a user to carry a handheld interface 8 between regions (see the dashed line 5 in FIG. 1) dedicated to each communications server 12. Optionally, when this occurs, the handheld interface 23, is considered to have signed off with the old communications server (as illustrated by the dashed line 22). Thereafter, the handheld interface 23 must be signed onto the new communications server (as illustrated by the line 24) before it may be used for data entry.

Figure 2:
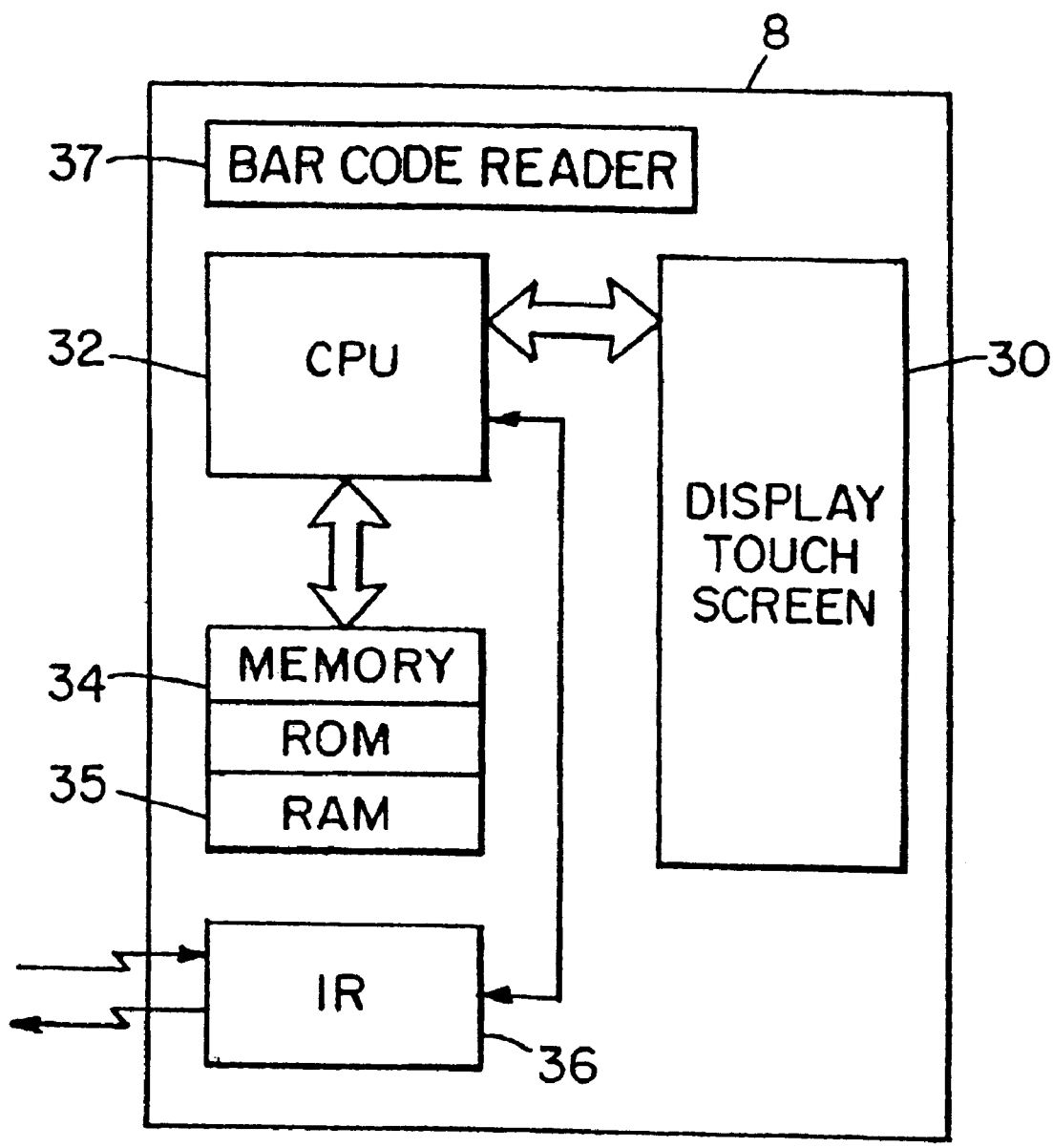
FIG. 2 illustrates a block diagram of a handheld interface according to the present

The manner by which these objects and functions are achieved will become clear in connection with the following explanation of each module of the present invention.
Handheld Interface FIG. 2 generally illustrates a block diagram of a handheld interface 8 having a display screen 30 which may be back-illuminated and which is controlled by a CPU 32 to display desired information thereon. The display screen 30 also functions as a touch pad and is sensitive to user contact. When contacted, the display screen 30 outputs a signal to the CPU 32 identifying the exact location of the contact therewith. The handheld interface 8 further includes a memory module 34 which stores software to control processing of the CPU 32 and which temporarily stores data received from, and transmitted to, the corresponding communications server 12. The CPU 32 controls an IR interface 36 to control data transmissions to and from the communications server 12. A bar code reader 37 is included to allow the user to enter customer or product information from a bar code, such as customer/patient ID and the like.

As explained below, the handheld interface 8 operates as an "event driven" device wherein the touch screen 30 is drawn to display a desired arrangement of virtual regions. Each region is assigned a unique identifier. The handheld interface 8 recognizes each contact by a user as an event. The contact/event is recognized with respect to the correspondingly defined region and the region identifier is returned. Thereafter, the CPU 32 identifies the necessary course of action based upon this identifier.

Figure 3:
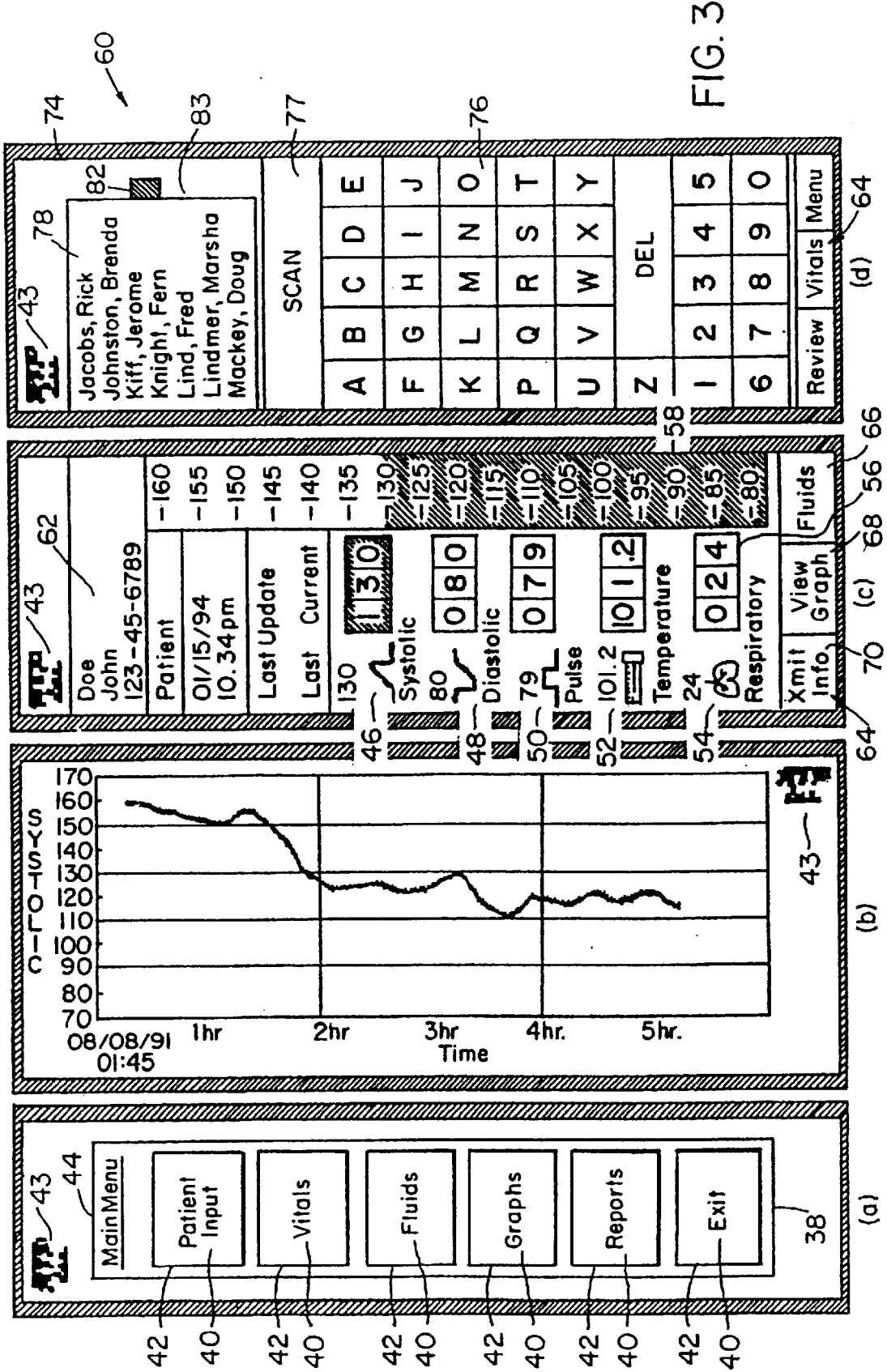
FIGS. 3(a), 3(b), 3(c), and 3(d) illustrate exemplary display screens shown on the handheld interface according to the present invention.
Figure 10:
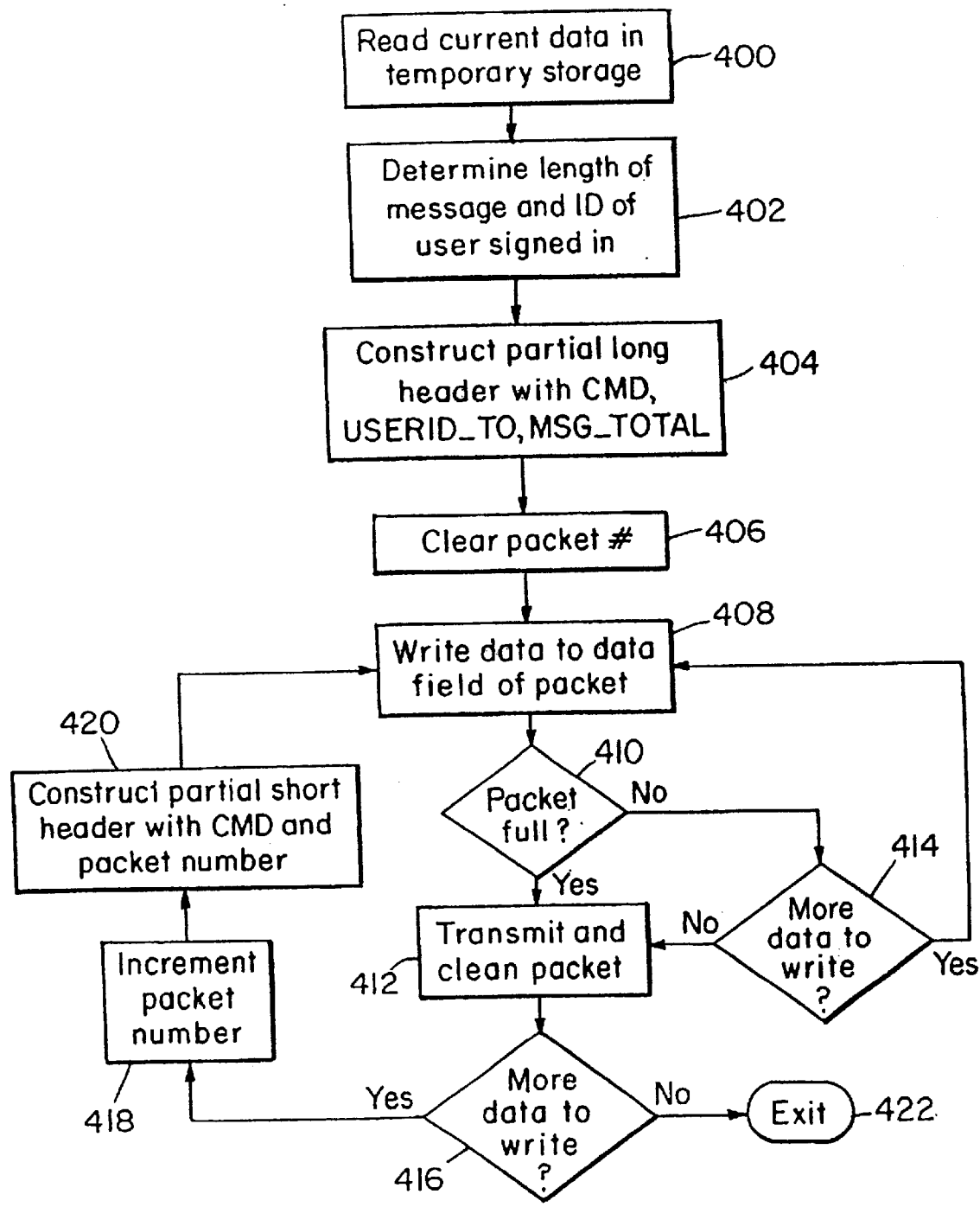
FIG. 10 illustrates the processing sequence undergone by the handheld interface to write data packets to the communications server.

As illustrated in FIG. 3, during operation the CPU 32 may display a variety of menus, graphs, and the like upon the touch screen 30. Within each display, the CPU 32 defines virtual regions which correspond to predefined processing sequences. The user initiates a desired event sequence by contacting the preferred region corresponding to the event. To facilitate the user interaction therewith, the CPU 32 provides multiple manners in which the user may enter and retrieve data. As illustrated in FIG. 3(a), the CPU 32 draws a main menu 38 on the screen 30 and defines multiple menu selections 40 therein (see the flowchart of FIG. 10). Each menu selection 40 overlays and corresponds to a virtual event region 42 corresponding to a different event/case. Every screen 30 is displayed with an escape key 43 which allows the user to escape back to a previous function/screen or back to the main menu.

Figure 13:
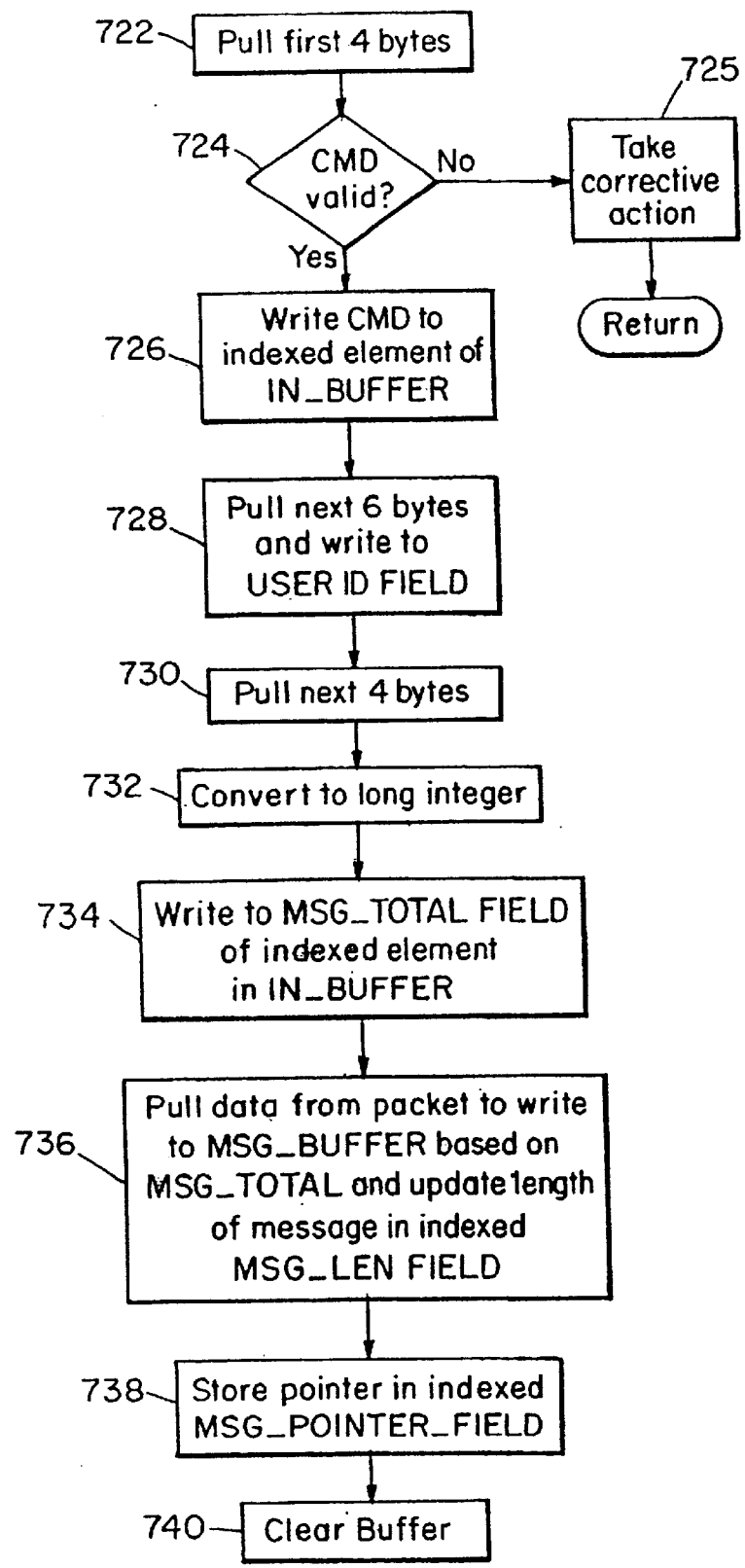
FIG. 13 illustrates the processing sequence by which the communication server parses through a long header structure within an incoming packet to build the input buffer.

When implemented in a healthcare application, as illustrated in FIGS. 3a–3d, when the user selects a vitals event region 44, the CPU 32 recognizes it as such and processes a corresponding event sequence (see FIG. 13).

As illustrated in FIG. 3c, the vitals input screen 60 (also referred to as the data I/O screen) displays current patient information in the patient field 62, such as the patient's name, social security number, status, and the date upon which the vitals were last updated. The vitals input screen 60 illustrates the last current vitals (data sets) as shown in the systolic field 46, diastolic field 48, pulse field 50, temperature field 52, and respiratory field 54 (collectively referred to as data fields). The touch screen 30 allows the user to activate a desired vital sign field by selecting a corresponding icon 46, 48, 50, 52, and 54, respectively. Located immediately above each icon is the current value for the corresponding vitals field. This current value is also displayed within three rolling keys along side of the icon (the rolling keys are designated by the reference numeral 56). The patient's systolic vital sign field is active in FIG. 3c, as evidenced by the inverted rolling keys 56. Proximate the rolling keys 56 is a scroll bar 58 for illustrating in a bar format the current value of the active vital sign field (i.e., systolic) which is inverted to the current level (130).

To enter new patient vitals, the user may do so in multiple ways. First, the user may update the patient's systolic vitals by consecutively contacting each rolling key 56 to be incremented. Each rolling key continuously increments, such as from 0 to 9 and then back to 0. Alternatively, the user may enter patient vitals information by contacting the scroll bar 58 at the desired position. In accordance with the flowchart of FIG. 13, when the user contacts the scroll bar 58, the bar is updated to reflect the newly entered value. If the user drags his/her finger along the scroll bar 58, the CPU 32 will continuously update the level thereof to reflect this movement of the finger. The CPU 32 updates the corresponding rolling keys 56 for the active field (i.e., the systolic field as illustrated in FIG. 3(c)). The user may drag his/her finger across the scroll bar 58 until the desired value is displayed in the rolling keys 56, at which time the user releases the scroll bar. The user may activate a different vital sign field (i.e., change the mode) by selecting the corresponding icon (46, 48, 50, 52, and 54).

The vitals input screen 60 further includes change function keys 64 which afford the user's direct access to displays, graphs, screens and the transmit function. More specifically, the vitals input screen 60 allows the user direct access to the fluids input screen (not shown) for the current patient by pressing the fluids function button 66. Alternatively, the user may view the selected vital sign field (e.g., systolic field) in a graph format by selecting the view graph button 68. The vitals input screen 60 further includes a transmit information button 70 which the user selects once a patient's new vital information has been entered. When the transmit button 70 has been pressed, the CPU 32 transmits the updated patient information to the communications server 12 in a format described below.

FIG. 3(*b*) illustrates a graph corresponding to the present patient's systolic vitals which is displayed when the view graph button 68 is selected.

FIG. 3(*d*) illustrates a patient inquiry screen 74 selected from the main menu 38 (also referred to as the data set inquiry screen). The patient inquiry screen 74 displays a scrolling text window 78 which exhibits the currently selected patient's name (data set header) and those names alphabetically proximate thereto. Along one side of the scroll text window 78 is positioned a scrolling bar 80 which includes an identifier 82 designating the position of the currently selected patient's name within a master alphabetical list. The user may scroll through the patient list by contacting the scrolling bar 80 at a desired location therealong. The top and bottom of the scrolling bar 80 corresponds to the beginning and end, respectively, of the list of patient names stored within the handheld interface 8.

The patient inquiry screen 74 also includes a virtual keypad 76 which allows the user to enter the name of a desired patient. As the user selects each letter of the desired patient's name, the CPU 34 automatically performs a search upon the entered letters and updates the scroll text window 78 correspondingly. As the user enters additional letters, the CPU 32 concatenates these letters to the end of the search string it uses and again updates the scrolling text window 78. The patient inquiry screen 74 also includes function buttons 64 along a bottom thereof to allow the user to automatically jump to an alternative screen. A scan button 77 is included to allow the user to read bar code data from a patient's wrist band, such as patient ID.

Figure 18:
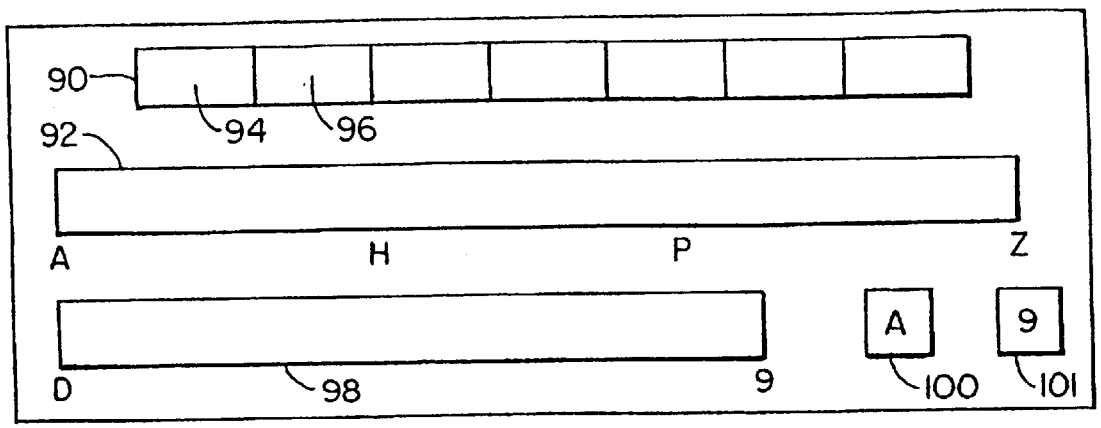
FIG. 18 illustrates an alternative data entry display for the handheld interface.

FIG. 18 illustrates an alternative scroll bar implementation which may be used to allow the user to enter alphanumeric information. For instance, the CPU 32 may control the display screen 30 to illustrate a display field 90 and one or more scroll bars 92. The scroll bar 92 may be defined such that one end corresponds to the letter A while the opposite end corresponds to the letter Z. The CPU 32 would define multiple regions along the length of the scroll bar 92, each region corresponding to one letter of the alphabet. When the user contacts the scroll bar 92, a letter corresponding to the touched regions is displayed in a first location 94 of the display field 90.

As the user drags his/her finger along the scroll bar, the letter displayed within the first location 94 will vary correspondingly to the currently selected region. Once the user removes his/her finger from the scroll bar 92, the last identified region is designated as the correct letter and entered in the first location 94 of the display. When the user again contacts the scroll bar 92, the CPU 32 operates to display a corresponding letter in the second field location 96 of the display field 90.

If it is desirable to enter numerals within the display field 90, the CPU 32 may also draw a second scroll bar 98 upon the display screen 30. The first end of the second scroll bar would represent a 0 while the second end of the scroll bar 98 would represent a 9. The user would enter numerals in the display fields 90 in the same manner as discussed above with respect to letters. Optionally, a single scroll bar may be provided for letters and numerals with function buttons 100 and 101 being used to assign letters or numerals to the scroll bar.

Figure 15:
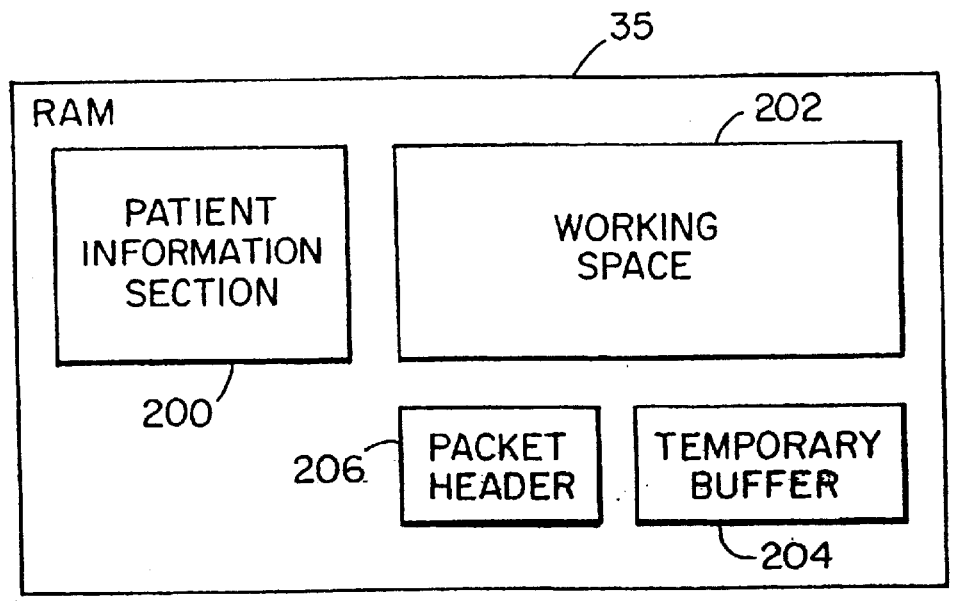
FIG. 15 illustrates the processing sequence by which the communication server generates the processing queue.

FIG. 15 illustrates the RAM section 35 of the memory within the handheld interface 8. The RAM memory 35 includes a patient information section 200 for storing a list of patient names (data set headers) and patient identifiers (data set identifiers) associated with the present user of the handheld interface 8. The RAM memory 35 also includes a working space 202 for storing all other information entered by the user and transmitted between the handheld interface 8 and the communications server 12. Each time the CPU 32 transmits a request to the communications server 12 for patient information, the CPU 32 redefines the current data structure within the working space 102 to correspond to the expected format of the return data from the communications server 12.

By way of example only, when the CPU 32 requests patient vitals, it expects the returned data to include, in a preset order, the patient's social security number, date on which the patient vitals were last updated, and the most recent systolic, diastolic, pulse, temperature and respiratory values. The CPU 32 sets up fields within the working space 202 for each of these values. When the returned data is received, the CPU 32 parses through the returned packet and assigns bytes therefrom to the desired field in the working space 202.

The RAM 35 further includes a temporary buffer for storing incoming and outgoing packets of information which are to be transmitted to and which are received from the communication server 12. The CPU 32 moves data from the RAM 35 into the temporary buffer 204 immediately before transmitting this information and adds a packet header 206 thereto.

FIGS. 4–8 illustrate the processing sequence by which the CPU 32 controls the main menu, vital sign patient/data set input screen and the patient information screen (FIGS. 3*a*–3*d*).

Figure 4:
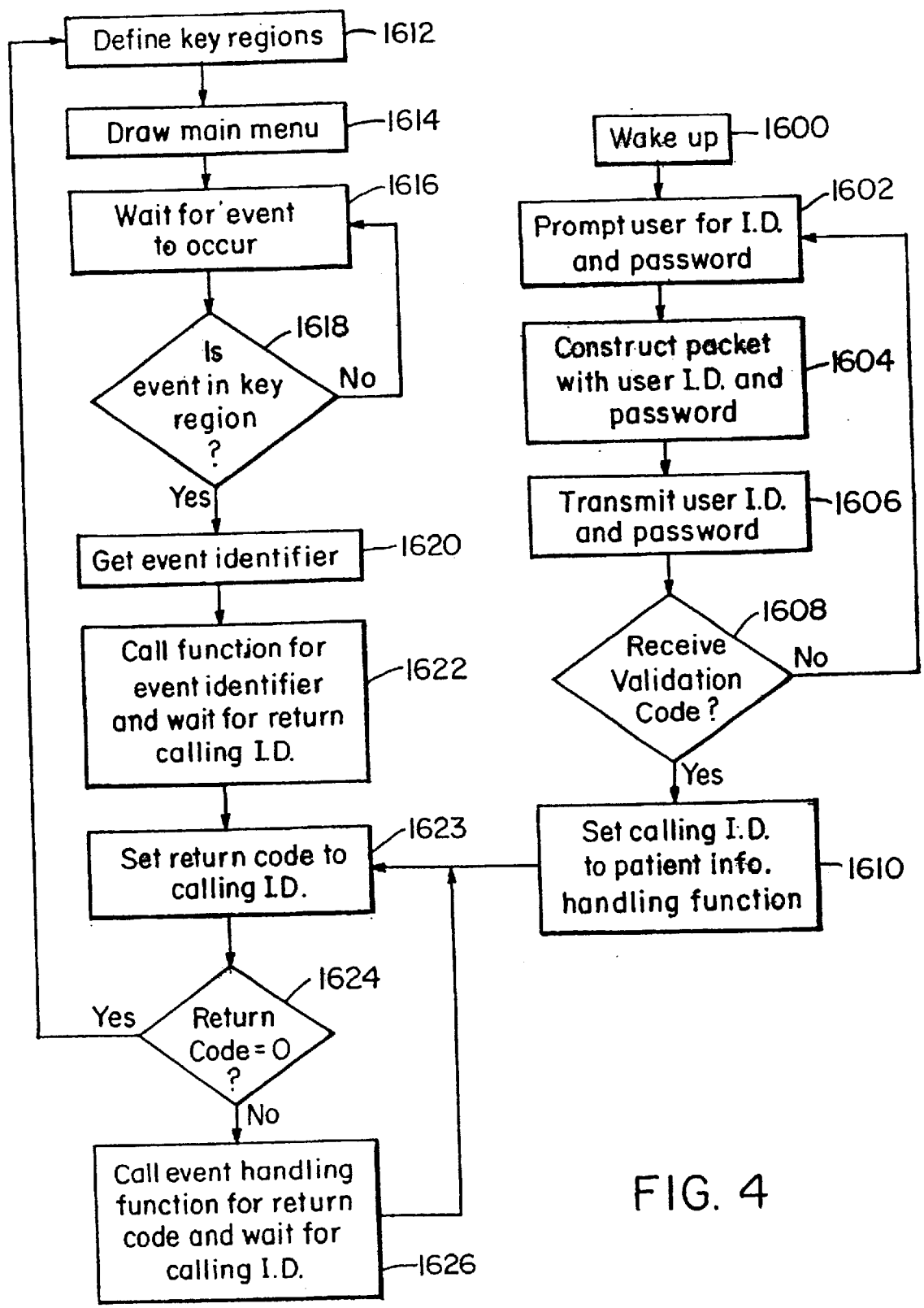
FIG. 4 illustrates the main processing loop by which the handheld interface monitors and responds to events selected by the user.

Generally, during operation the CPU 32 loops through one of two primary case/event handling loops (FIG. 4). The first case/event loop operates to draw the main menu (FIG. 3*a*) and to handle events chosen from the main menu. When an event occurs which corresponds to a defined key region within the main menu, a corresponding event identifier is returned as the calling identifier. A return code is set equal to this calling identifier and the return code is checked against a predefined value (0). If the return code is non-zero, processing flow enters the second primary loop to call the corresponding event handling function. The second primary loop corresponds to processing in which a menu other than the main menu is displayed (FIGS. 3*b*–3*d*). During this second loop, a code which identifies the next function to be performed is continuously checked. When the code equals zero, processing returns to the main loop. When the code is a nonzero value, the corresponding function is called. Once each function is completed it returns a code identifying the next function to be performed by the user. This configuration reduces the memory requirements by reducing the levels of functions to be called, thereby reducing the necessary stack space.

FIG. 4 generally illustrates the processing undergone by the handheld interface 8 when the user initiates the first session (i.e., when the user first logs in). When a session is initiated the handheld unit prompts the user for the user's ID and password (step 1602). Next, a packet is constructed in the temporary buffer 204 which contains a long header 206 structure and has a data section including the user ID and password (step 1604). This packet is transmitted (step 1606) and a validation code therefor is waited upon. If the validation code is not received (step 1608) processing returns to step 1602 in which the user is reprompted for the ID and password. If a validation code is received, processing continues to step 1610 in which a return code is set to indicate that processing should move to the patient inquiry module. Thereafter, the return code is tested to determine whether it equals zero (step 1623). If the return code equals zero, processing returns to step 1614 in which the main menu is redrawn.

After this initial login sequence is completed, flow enters the main event handling loops. First, a main menu is drawn and key regions therein are defined in steps 1612 and 1614, after which the system waits for an event to occur (step 1616). Once an event occurs, it is determined whether the event is within a defined menu regions 42 (step 1618) (i.e., whether the user has touched the display screen 30 at a location corresponding to a menu selection 40). If not, processing loops back to wait for the next event. If so, an event identifier is obtained for the key region in which the event occurred (step 1620). Next, an event handling function corresponding to the event identifier is called (step 1622). Thereafter, processing waits for a call identifier returned from the called event handling function. A return code is set equal to the call identifier (step 1623) and the return code is tested in step 1624 and if zero, processing returns to the initial step 1612 to redefine and redraw the main menu. If the return code does not equal zero, the process determines that the user has selected another function besides displaying the main menu. Thus, the event handling function corresponding to the non-zero return code is called (step 1626). Thereafter, the main event handling loop waits for the called function to return a call identifier which is tested in step 1624.

Figure 5:
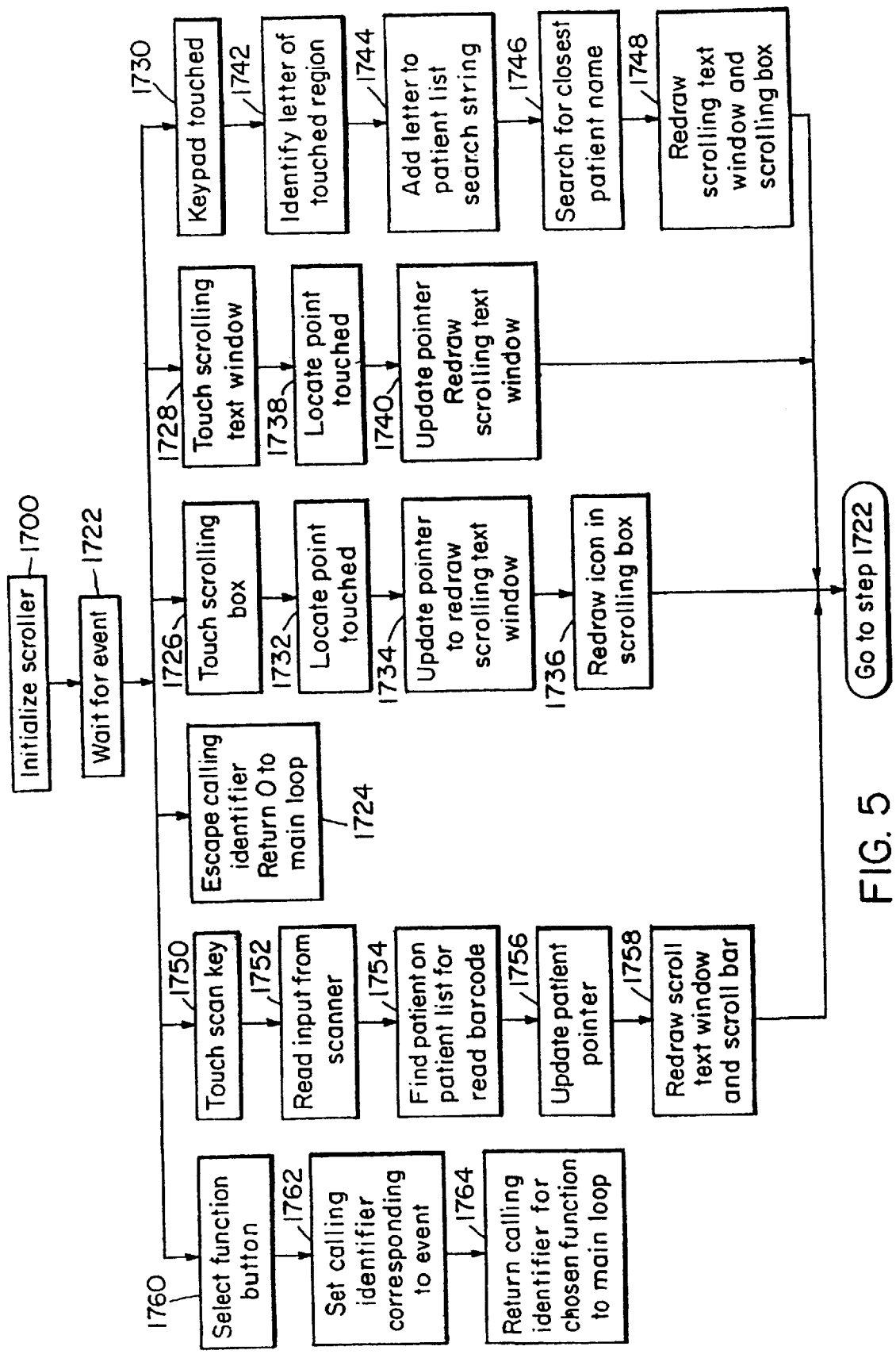
FIG. 5 illustrates the processing:sequence of the handheld interface while displaying a patient information screen.
Figures 6, 8:
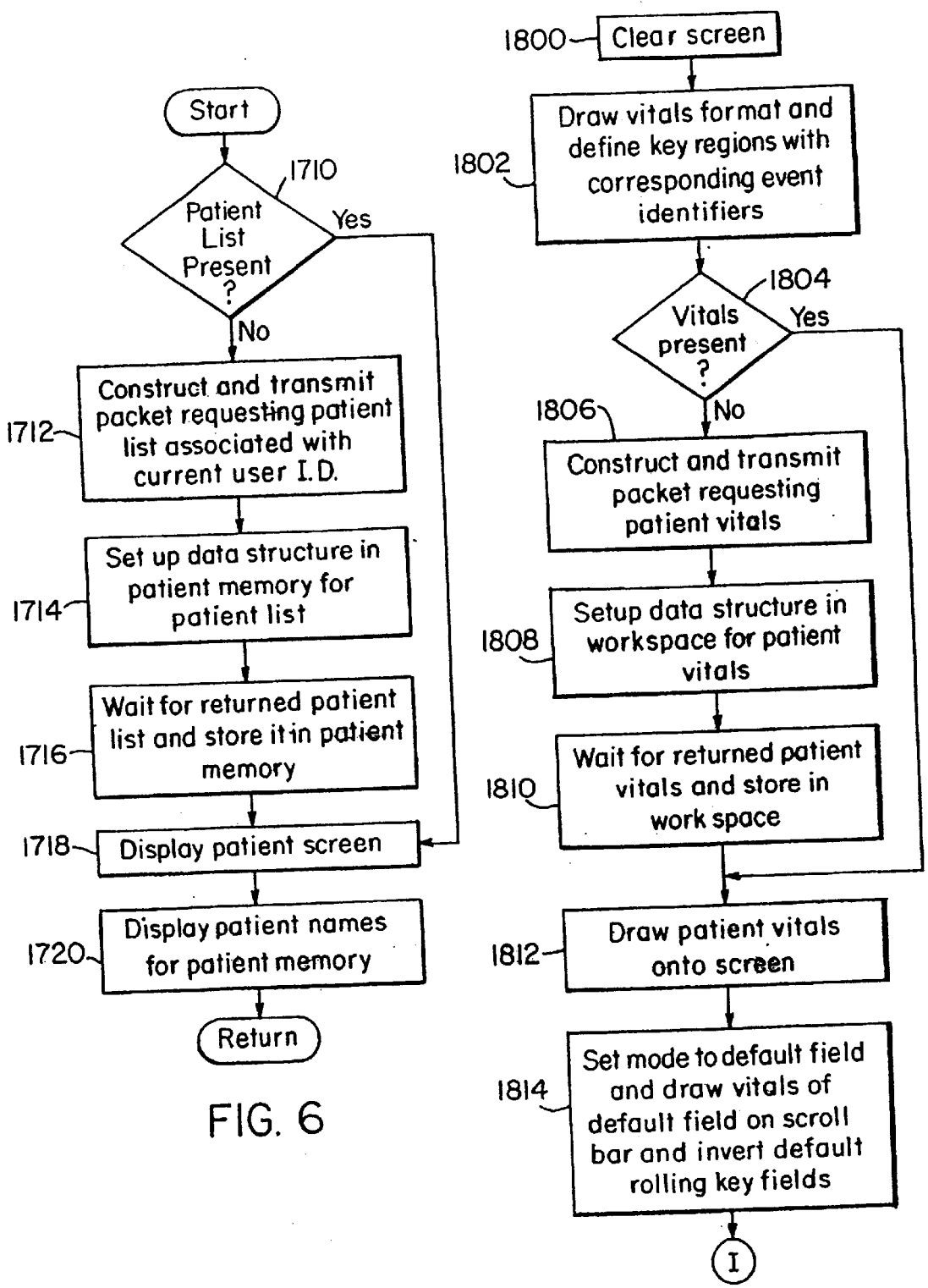
FIG. 6 illustrates the processing sequence of the handheld interface to initiate the patient information screen.
FIG. 8 illustrates the processing sequence of the handheld interface to initiate the patient input screen.

FIGS. 5 and 6 illustrate the process undergone when the patient information screen 74 is selected to be displayed (such as during the wake up function or when called by the user). First, an initialization routine is called in step 1700 (steps 1710–1720 in FIG. 6). This initializing process begins by determining whether the handheld interface 8 includes a list of patient names (data set headers) and IDs (step 1710). If this list does not exist (such as when the handheld interface has initially been woken up), the unit constructs and transmits a packet to the communications server 12 requesting the patient list associated with the currently signed-in user (step 1712). The communications server 12 receives this packet, identifies the user ID, and requests the appropriate information from the command server 14. Thereafter, the appropriate database 16 is read and the patient list for the user is transmitted back to the handheld interface 8. After the interface 8 sets up the data structure in the patient memory 200 for the patient list (step 1714), it waits for the returned patient list (step 1716). Once the patient list (name and ID) is received, it is stored in the patient memory 200.

The handheld interface 8 may not include sufficient display space in the scrolling text window 78 to show an entire patient's name. Thus, the patient memory section 200 will only include sufficient memory to store the maximum number of characters which may be displayed for a single patient name upon the screen. Once the patient list is stored, the patient screen format is displayed (step 1718) as illustrated in FIG. 3*d*. Next, the patient names are displayed in the scrolling text window 78 (step 1720) (FIG. 3*d*). When the patient list is too long to be completely displayed within the scrolling text window 78, a default portion thereof is displayed. Next, the system waits for an event (step 1722, in FIG. 6) and when one occurs, an event identifier is assigned thereto.

The event identifier is passed to a case/event statement which includes every possible valid value for the event identifier. By way of illustration, processing will continue along one of six possible processing paths to blocks 1724, 1726, 1728, 1730, 1750 or 1756, depending upon which event occurred. When event 1724 occurs (i.e., the user presses the escape icon), the system returns a zero calling identifier to the main loop (thereby indicating that no new event handling function has been selected). If the event indicates that the user has touched the scrolling bar 80, processing flows to box 1726 in which the system determines the exact location of the event (step 1732). This location is correlated with a pointer that is used as an index into the patient list to identify the new patient to be displayed in the scrolling text window 78. Once the event location is-determined, the pointer into the patient list is updated and the scrolling text window 78 is redrawn to display the name of the selected patient and a limited number of patient names surrounding the selected name (step 1734).

Next, the scrolling bar 80 is updated to move the identifier 82 to a new position identifying the relative location of the indexed patient within the overall patient list (step 1736). Thus, if the first patient is selected, the identifier 82 is redrawn at the top of the scrolling bar 80, and if the last patient is selected, the identifier 82 is drawn at the bottom of the scrolling bar 80. If the event is identified as occurring within the scrolling text window 78, processing flows to step 1728. Specifically, the location of the event is again identified (step 1738) relative to the names currently displayed. The name closest to the event is identified as the selected patient. Thereafter, the pointer into the patient list is updated to index the newly selected patient name (step 1740). This name is displayed in the center of the scrolling text window and, optionally, may be inverted in color (step 1740). The identifier 82 within the scrolling bar 80 is also redrawn to properly identify the new position of the selected patient within the patient list (step 1740).

If the keypad 76 is touched, processing flows to block 1730, at which the letter is identified which corresponds to the region touched (step 1742). This selected letter is added to a temporary patient searching string within the work space memory 102 (step 1744). This letter is added to a search string (which is empty until the first letter is selected). Thereafter, the processor conducts a search based-upon the search string into the patient list to identify the name most closely corresponding to the letter(s) selected from the virtual keypad 76 (step 1746). If a search string exists (i.e., the user has already entered some letters) the newly selected letter is concatenated onto the search string and a new search is conducted upon the text strings within the patient list to find the first text string which is greater in alphabetic value than (i.e., closest to) the search string. The pointer is set to the closest patient name and the scrolling text window 78 and the scrolling bar 80 are updated (steps 1746 and 1748). If the user wishes to delete a letter from the search string, he/she simply pressing the delete region key.

If the user selects the scan region 77, processing flow moves to block 1750. The bar code scanner is read to obtain the bar code scanned by the user (step 1752) (this bar code may appear on a patient's wrist band and the like). The bar code includes the patient ID, which is used to find the patient name within the patient list (step 1754). Next, the pointer into the patient list is updated (step 1756) and the scrolling text window 78 and scrolling bar 80 are redrawn (step 1758).

Once the user has selected a desired patient, the user may escape from the patient inquiry screen by pressing the escape icon 43 in the upper left corner or by selecting one of the function 64 buttons at the bottom of the screen (step 1760). As illustrated in FIG. 3d, the user may escape to the main menu, review a patient's information complete record or review the patient's vitals. If the user presses one of the change function buttons 64 at the bottom of the screen, the corresponding event identifier is evaluated to determine which function key the user has selected (step 1762) and the corresponding return code is returned to the main processing loop in FIG. 16 (step 1764).

Figure 7A:
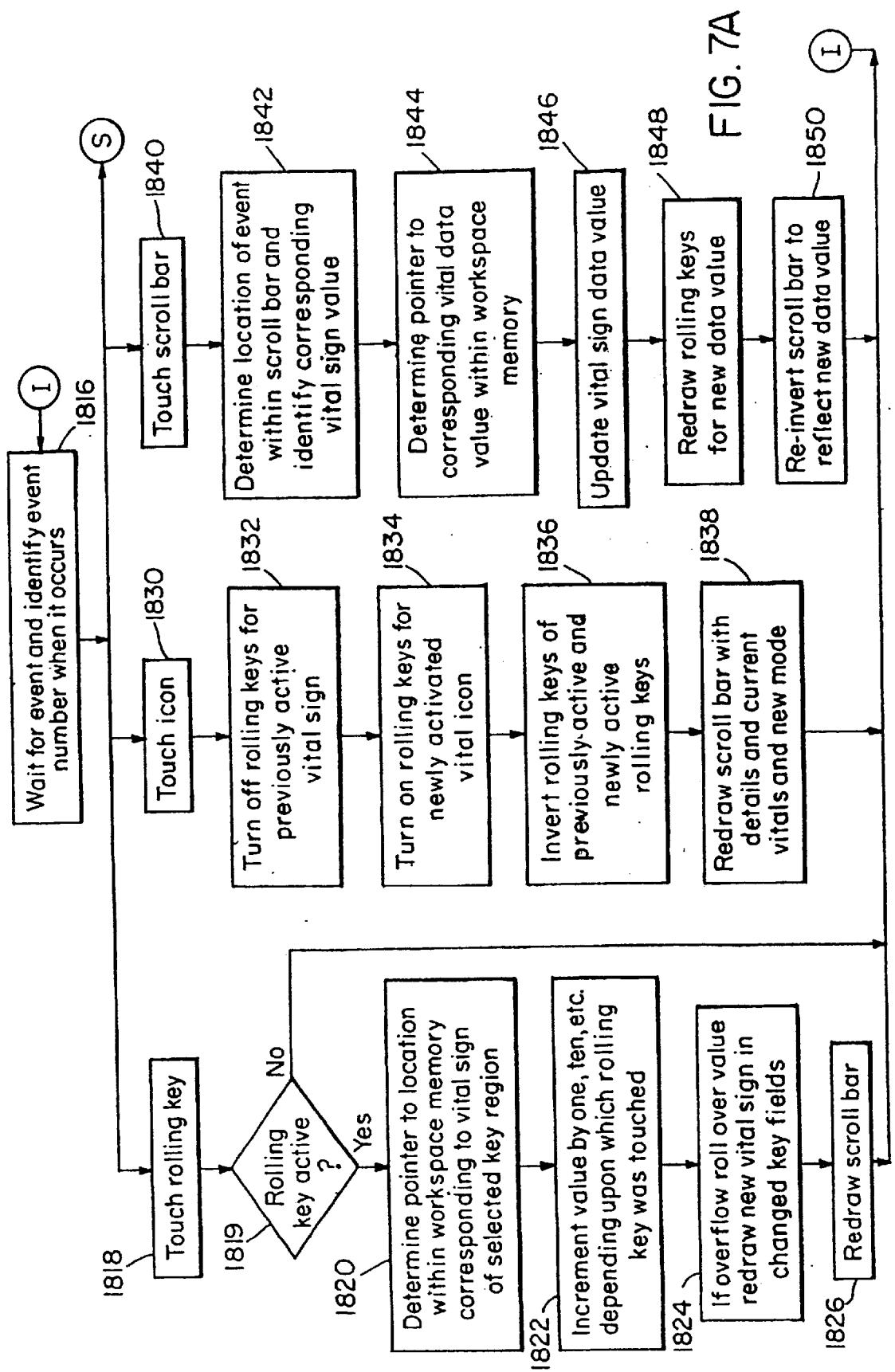
FIGS. 7(a) and 7(b) illustrate the processing sequence of the handheld interface while displaying a patient input screen.
Figure 7B:
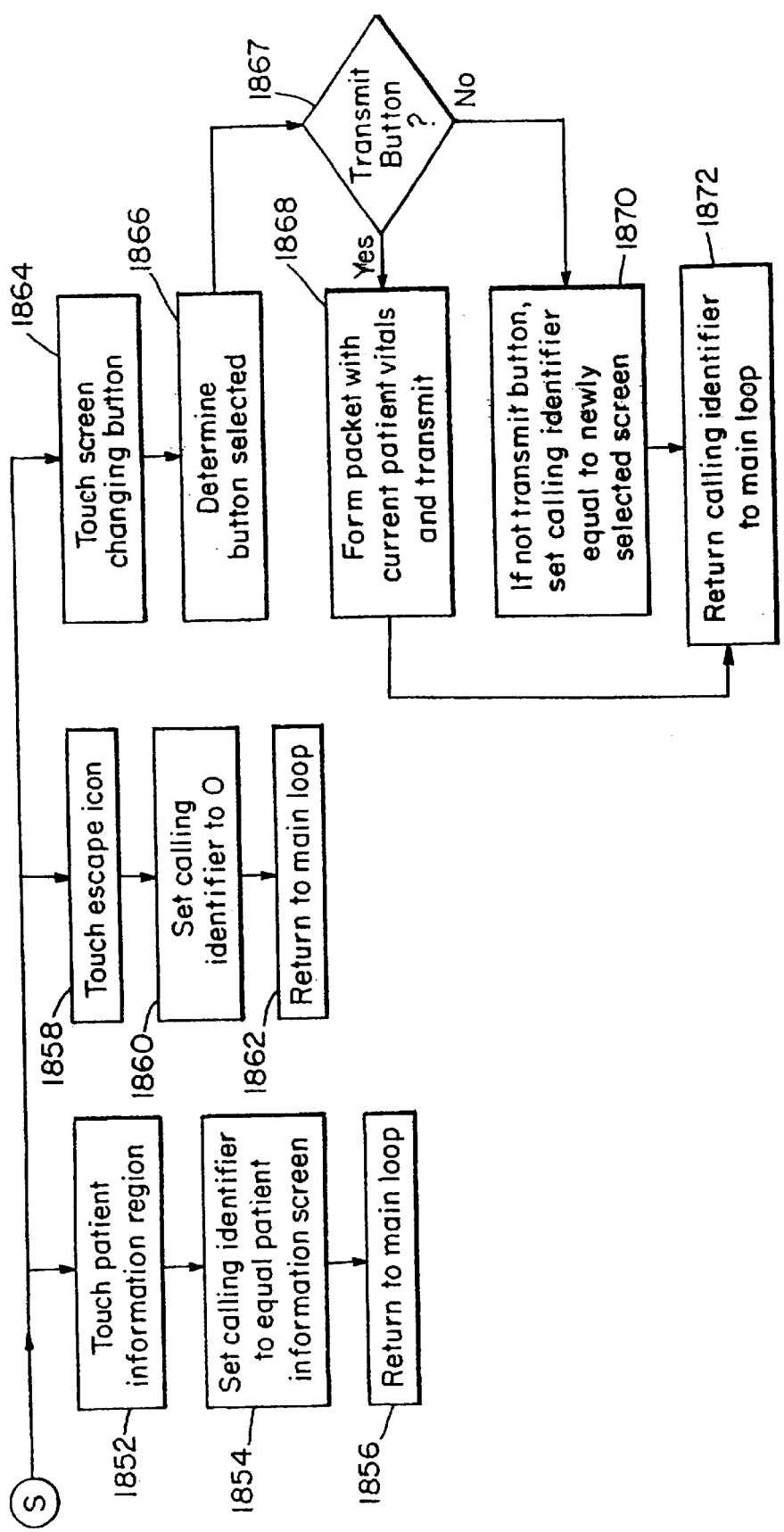

FIGS. 7a, 7b and 8 illustrate the processing sequence undergone by the handheld interface 8 when the vitals/data input/output handling function is chosen (i.e., when a user desires to enter patient vitals). First, the display screen is cleared (step 1800) and the vitals (data I/O) format is drawn upon the screen (step 1802). Similarly, the key regions are defined which correspond to each even identifier. Next, it is determined whether the workspace memory contains vitals for a selected patient (step 1804). If not, the processor constructs and transmits a packet (step 1806) requesting patient vitals. Thereafter, the workspace memory 202 is set up in the data structure corresponding to patient vitals (step 1808). Thereafter, the handheld interface waits for the returned patient vitals, receives these vitals in one or more packets and disassembles the packets and stores the patient vitals in the workspace (step 1810). Next, the processor draws the patient vitals onto the screen (step 1812) and sets the default mode to a predetermined field (e.g., systolic field). The vitals for the default field are drawn into the scroll bar (step 1814) and the default rolling keys 56 corresponding to the default field are inverted. Thereafter, the handheld interface waits for an event to occur (step 1816 in FIG. 7a) and when it occurs, identifies the event number corresponding thereto.

Processing flows along one of six paths depending upon which event number is identified. While each field upon the vitals screen corresponds to a separate event number, the events as displayed in FIG. 8 may be grouped into six general categories, namely, touching a roll key, touching the icon, touching the scroll bar, touching the patient's general information, touching the escape key, and touching the change screen buttons (blocks 1818, 1830, 1840, 1852, 1858 and 1864). Once the event number is identified as corresponding to a rolling key 56, it is determined whether the touched rolling keys are active (step 1819). If not active, processing returns to step 1816. If active, a pointer is determined which identifies the field within the workspace memory 202 which corresponds to the specific roll key/vital sign selected (step 1820).

Next, the data value identified by the pointer into the workspace is incremented by a 1, 10, 100, etc. depending upon the rolling key which was touched (step 1822). Thus, referring to FIG. 3c, if the user presses the center rolling key corresponding to the systolic field, the systolic data value within the workspace memory will be incremented by 10. Similarly, if the diastolic field is selected and the user presses the leftmost rolling key therein, the processor will increment the diastolic data value within the workspace memory by 100. Next, it is determined whether or not the incremented value has created an overflow and if so, the incremented digit is rolled-over (step 1824). This rollover function is performed to rotate a rolling key having a current value of 9 to a new value of 0.

Thus, if the user selects the pulse vital and contacts the "1s" rolling key (which has a present value of 9), the processor will update the pulse value within the workspace memory to "80". Thereafter, the new vital sign is drawn into the rolling keys 56 which have been updated and the new vital sign is stored in the corresponding field in the workspace memory (step 1824). Finally, the processor updates the scroll bar 58 to reflect the change in the current data value (step 1826).

If the event identified in step 1816 corresponds to an icon, processing proceeds to step 1830. First, the rolling keys are deactivated for the previously active vital sign field (step 1832) and the rolling keys for the newly chosen vital sign are activated (step 1834). Next, the rolling keys for the deactivated and newly activated vital sign fields are inverted to display the newly active field to the user (step 1836). Thereafter, the scroll bar 80 is redrawn with parameters, ranges and current vital signs corresponding to the newly selected vital sign field (step 1838).

When the identified event corresponds to touching the scroll bar 80, process flows to step 1840. Once the scroll bar is touched, the exact location of the event is determined therein and used to identify the corresponding vital sign value (step 1842). Then, a pointer is determined which identifies the vital sign data value within the workspace memory which corresponds to the active vital sign field (step 1844). This vital sign data value is updated to the new vital sign value selected within the scroll bar (step 1846). Thereafter, the active scroll keys are updated with the new data value (step 1848) and the scroll bar is inverted to reflect the new data value (step 1850). When the event occurs within the patient information region, processing flows to step 1852. In such a case, the patient information screen is redrawn. To do so, a calling identifier is set to correspond to the patient information screen (step 1854) and control is returned to the main loop (step 1856).

Optionally, when the user touches the patient information region, a pop-up window may appear and query the user as to whether it is desirable to go to the patient information screen or enter a patient identifier through the bar code reader. In either case, if the user touches the patient information region, before new patient vital signs have been transmitted to the communication server, the user is prompted as to whether or not these vital signs should be transmitted. When the escape icon is touched, processing flows to step 1858, after which the calling identifier is set to zero (step 1860). Processing is returned to the main loop (step 1862).

If the screen changing buttons are touched, processing flows then to step 1864, after which the selected button is determined (step 1866). In step 1867, it is determined whether the event corresponds to the transmit button. If the selected button corresponds to the transmit button, the current patient vitals are constructed into a packet format and transmitted to the communication server 12 (step 1868). If the selected button does not correspond to the transmit button, the calling identifier is set equal to the newly selected screen (step 1870). Thereafter, control is returned to the main loop (step 1872).

When the return code within the main loop is set to correspond to the view graph display screen (FIG. 3d), the processor determines the active vital sign field (e.g., systolic field), and obtains the corresponding default parameters for the graph. Thereafter, the screen is cleared and a graph having the parameters for the active vital sign field is drawn. Next, the vital sign data values for the active vital sign field are read from the workspace memory and used to draw the graph.

Optionally, in the view graph screen a series of changing function buttons may be displayed along the bottom thereof. These buttons would allow the user to automatically select another vital sign to view in a graph format without intermediately returning to the vital input screen.

In accordance with the above procedure, the handheld interface 8 allows for user inputs and displays patient information to the user.

Interface-Server Protocol

Once the user enters the desired data and wishes to send this data to the communications server 12, the user presses the transmit function button 70. Once the CPU 32 identifies that an event has occurred which corresponds the transmit function button 70, the main loop (FIG. 4) calls the transmit handling function. FIG. 4 illustrates the process by which the CPU 32 transmits data to the communications server 12.

Figure 9:
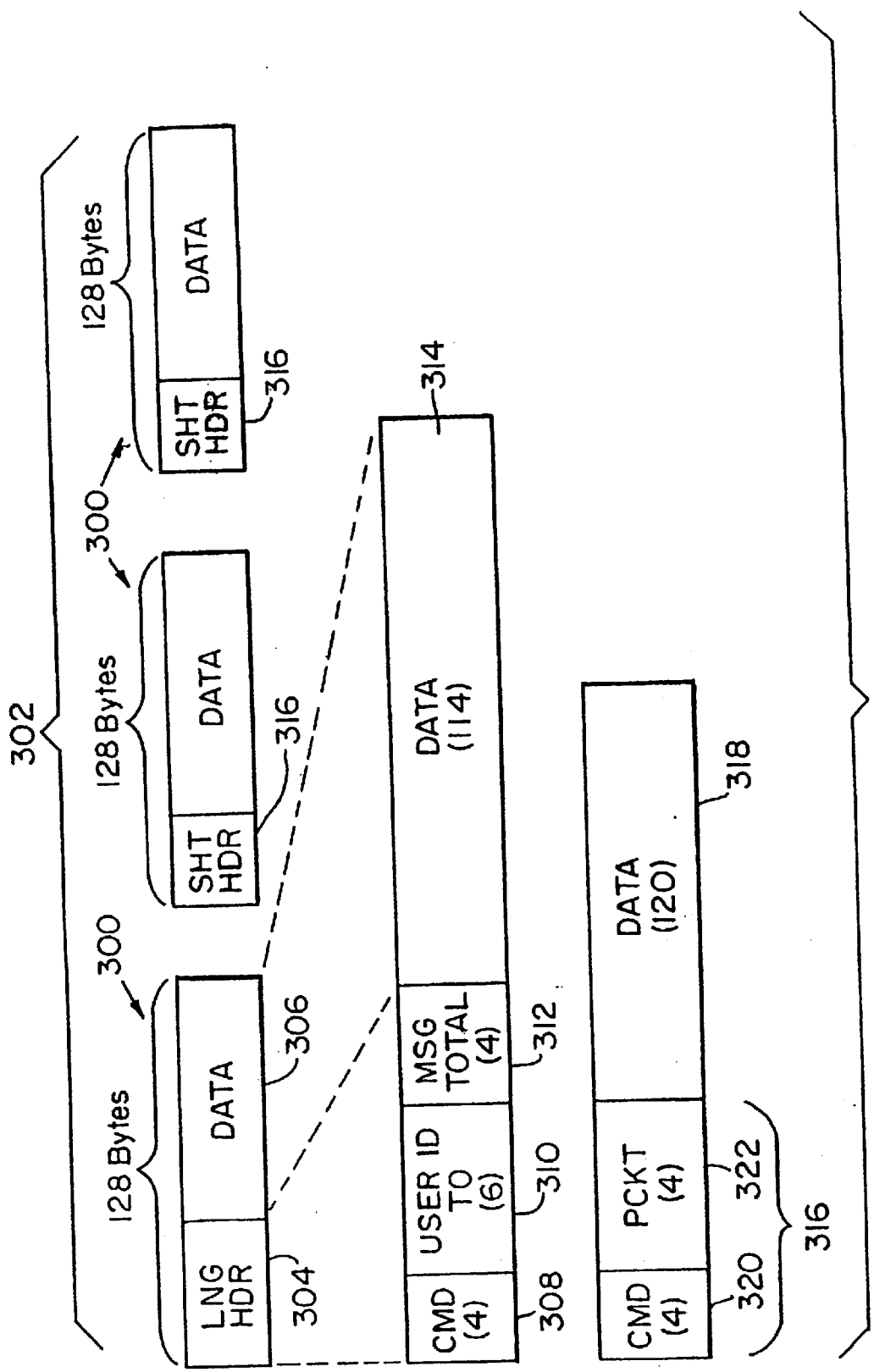
FIG. 9 illustrates the data structure of the packets transmitted between the handheld interface and the communications server.

As illustrated in FIG. 9, each transmission comprises an information packet 300 of IR signals corresponding to a packet of data, wherein every packet is constructed with the same predetermined length (e.g., 128 bytes) and in one of two formats. This length is software and operative system definable and may vary. Certain messages transmitted between the handheld interfaces 8 and the corresponding communication servers 12 comprise an amount of data which is unable to be assembled into a single packet. Thus, in such circumstances the transmitting device segments the data into a plurality of equal length packets 300 (referred to as frames). The series of frames form a message 302.

When transmitting a message the first packet/first frame thereof is constructed with a header section 304 formed in a long header structure followed by a data field 306. The long header 304 includes a 4 byte command field 308, a 6 byte user identifying field 310, and a 4 byte message total field 312. The command field 308 identifies the process to be performed upon the subsequent data, the user ID identifies the user signed into the handheld interface 8 transmitting or receiving the packet 308 and the message total 312 identifies the total length of the message which will follow. This total length includes all bytes within subsequent packets 300 corresponding to this specific message 302. Thereafter, a data field 314 (having 114 bytes in a packet with a 128 byte structure) follows.

If the message includes more data than will fit in a single packet, subsequent packets/frames are transmitted. These subsequent packets/frames are constructed with a short header structure 316 preceding the data segment 318. The short header 316 includes a 4 byte command 320 and a 4 byte positioning packet 322 identifying number to enable the receiving device to determine the position of the packet within the overall message. Packets containing a short header 316 includes a 120 byte data field for a packet formed with 128 bytes. During transmission, the first packet of each message includes a long header 304 structure followed by a data field, with each subsequent packet within the message including a short header 316 structure followed by a data field. In this manner, the device is able to increase the amount of data transmitted within each packet for long messages. The transmitting device need not send the user ID and the message total more than once for a given message since the receiving device is able to associate corresponding packets with a single message 302 based on the packet number 322 and communication channel.

To transmit a message (FIG. 10), the CPU 32 reads the current data from the workspace memory 200 in the RAM 35 (step 400). Next, the CPU 32 determines the length of the message and the ID of the user signed in to that handheld interface 8 (step 402). The CPU 34 constructs a packet header formed with the long header structure (step 404). The CPU 34 clears the packet number (step 406) and writes the data to the transmit buffer (step 408). If the packet is full (step 410), the CPU 32 transmits the packet and clears the buffer (step 412). If the packet is not full, it determines if more data exists to write to the buffer (step 414). If no more data exists, it transmits the packet. If more data exists, it again writes to the packet. In step 416, it is determined if more data exists, and if not it exits. If so, the packet number is incremented (step 418). Next, the CPU 34 constructs a partial short header for the second frame to be transmitted in this message (step 420). The partial header includes the code for the corresponding command and the current packet number. Thereafter, the next segment of data is written to the packet (step 408) and steps 410 through 420 are repeated. Once the last packet is transmitted (step 414) and it is determined that no more data remains to be written to the packet (step 416), the system exits the transmit routine (step 422).

Communication Server

Figure 16:
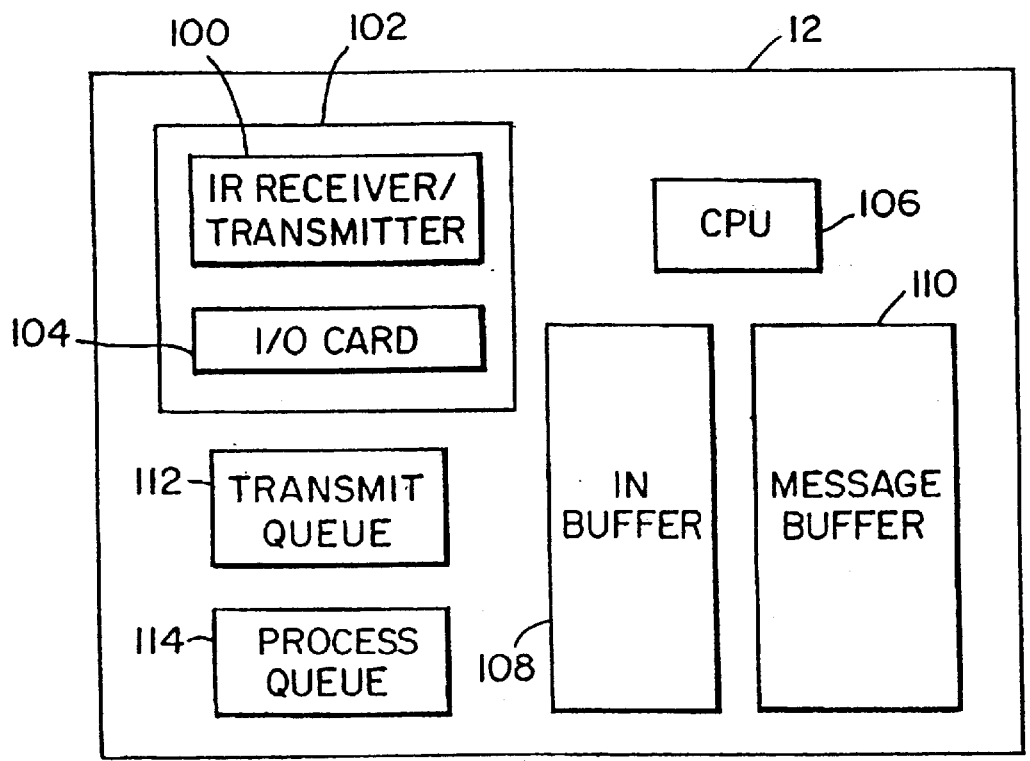
FIG. 16 illustrates a block diagram of the RAM section of the handheld interface.

FIG. 16 illustrates a block diagram of the communication server 12. The communication server 12 includes an IR receiver/transmitter 100 which receives and transmits IR communication packets from and to the handheld interface 8. The IR receiver transmitter 100 operates in conjunction with an I/O card 102 to store a packet of information from each communication channel in the corresponding address within a temporary buffer 104. Each communication channel corresponds to a unique handheld interface 8. For instance, the communication server 12 may provide for 128 IR channels and thus, the temporary buffer 104 will include 128 buffer locations, with each buffer location having sufficient memory to store a complete IR packet 300 (FIG. 9). The number of channels is locally definable and may be any desired number. The array locations within the temporary buffer 104 store the IR packets in the format transmitted from the handheld interface 8 as described above.

The communications server 12 further includes an input buffer 108 which represents a storage space used by the CPU 106 when converting packets from the format stored in the temporary buffer 104 to message lists with a different format to be transmitted to the command servers 14. The input buffer 108 represents an array, each element of which includes the COM_INFO structure (explained below).

Each element of the input buffer 108 array is accessed based on the device number. Thus, if 128 handheld interfaces 8 are being used, the input buffer 8 will include 128 elements.

The communications server 12 further includes a message buffer 110 which is utilized to store the actual data for each complete message sent from the hand held interface once all of the necessary packets have been transmitted by the handheld interface 8 and reassimilated by the CPU 106 into a single message. The COM_INFO stored in the input buffer 108 includes a pointer MSG_From_HH into the message buffer to the beginning of the corresponding data string. Once every packet 300 for a message 302 is received and the corresponding data is stored in the message buffer and the COM_INFO is stored in the input buffer 108, the CPU 106 constructs a message list therefrom. Each message list to be processed by the command server 14 is stored on one of a process queue 114. The message list includes a pointer to the corresponding data string in the message buffer 110. Each message list received from the command server 14 is initially stored in a transmit queue 116 prior to being converted back into packets 300 and transmitted to the handheld interface 8. The message list includes a pointer to a corresponding data string which is stored in the message buffer 110 when it is received from the command server 14.

The process and transmit queues are operated in a first-in-first-out sequence such that each message is processed or transmitted in the order in which it is placed in the queue.

The transmit and process queues 112 and 114 constitute dynamic queuing systems which attach message lists in a linked list structure. Each message list includes the data structure illustrated below:

| MESSAGE LIST | | | | | |
|---|---|---|---|---|---|
| COM_INFO 10 | Data File (Integer) | Command (1) | MSG_TO_HH (Pointer) | MSG_LEN (Long Integer) | Prev MSG_LST (Pointer) |

| COM_INFO | | | | | | | |
|---|---|---|---|---|---|---|---|
| Device Number (Integer) | CMD (4) | Packet Number (Long Integer) | User ID To (6) | User ID From (6) | MSG Total (Long Integer) | MSG Length (Long Integer) | MSG From HH (Pointer) |

The message list data structure includes a first section COM_INFO dedicated to, and containing information concerning, messages received from the handheld interface 8. The next four fields represent fields which are created immediately before transmitting a message list to the command server 14 and another communications servers 12. The final field (Previous MSG_LST) is used as a pointer to the subsequent message list within the queue to be processed. The first section COM_INFO includes a device number uniquely identifying the handheld interface transmitting the message. The device number is generated by the I/O card 102 when the CPU 32 requests a packet 300 from the temporary buffer 104. The device number is produced depending upon the communications channel being accessed. The command (CMD) includes the structure of the CMD field transmitted in the header of each packet 300 (i.e., the 2 byte database ID, 1 byte command ID, and 1 byte reserved).

The command (CMD) represents the command to be processed in accordance with the corresponding message being transmitted to or from the handheld interface 8. The 4 bytes within the command are separated such that the first two bytes identify the database to be processed when performing the command, the third byte stores a number corresponding to the specific command to be performed, and the fourth byte is reserved. By way of example, with respect to the third byte, numerals 1–127 represent commands to be processed by the command server, while numerals 128–255 represent a command from the handheld interface 8. As noted above, the use of shorthand code numbers for specific commands reduces the amount of data to be transmitted to and from the handheld interface 8.

The Packet Number is a long integer which is incremented each time a packet is appended to a message on the input buffer 108. The User_ID_To is a 6 byte value added by the handheld interface 8 to identify a destination user. If set to zero, the destination is the communications server. The communications and command servers determine which server to send the command to. This value if non-zero will identify the user of a handheld interface 8 desiring to communicate therewith. The User_ID_From is a 6 byte value added once at login time. This user ID is assigned to the channel to identify who is logged in at that channel. This value is maintained until the person signs out. Thus, the user ID will only be transmitted once during a login session. The communications server 12 keeps track of each User ID signed onto handheld interfaces served by that communications server 12. The message total length (MSG_Total) is a value assigned by the handheld interface 8 or by the command server 14 when a message is transmitted. The message length (MSG_LEN) is a value updated by the short and long header parsing functions to keep track of the length of a message in the message buffer 110 as the packets for the message are added thereto. The message length field is initially tested by the communications server 12 when processing each packet in the temporary buffer 104 to determine if the packet is in a long or short header form. The message pointer field (MSG_From_HH) is a pointer into the message buffer to the location of the actual data message. The MSG_From_HH pointer is updated each time a new packet is appended to a message.

The message list structure includes the above COM_INFO structure as an addition to a Data_File field that represents an integer identifying the database, written from the COM_INFO structure, to be processed in connection with the corresponding command. The command (CMD) field represents a one byte command, written from the COM_INFO structure, to be processed. The MSG_To_HH field represents a message pointer used to point to the data compiled by the command server in connection with this message which will ultimately be sent to the handheld interface 8. The MSG_LEN field represents a long integer identifying the current length of the data corresponding to the message and stored in the message buffer. The Previous_MSG_LST represents a pointer pointing to the next message to be processed. The previous message pointer enables the system to accomplish dynamic queuing for the process and transmit queues.

Figure 11:
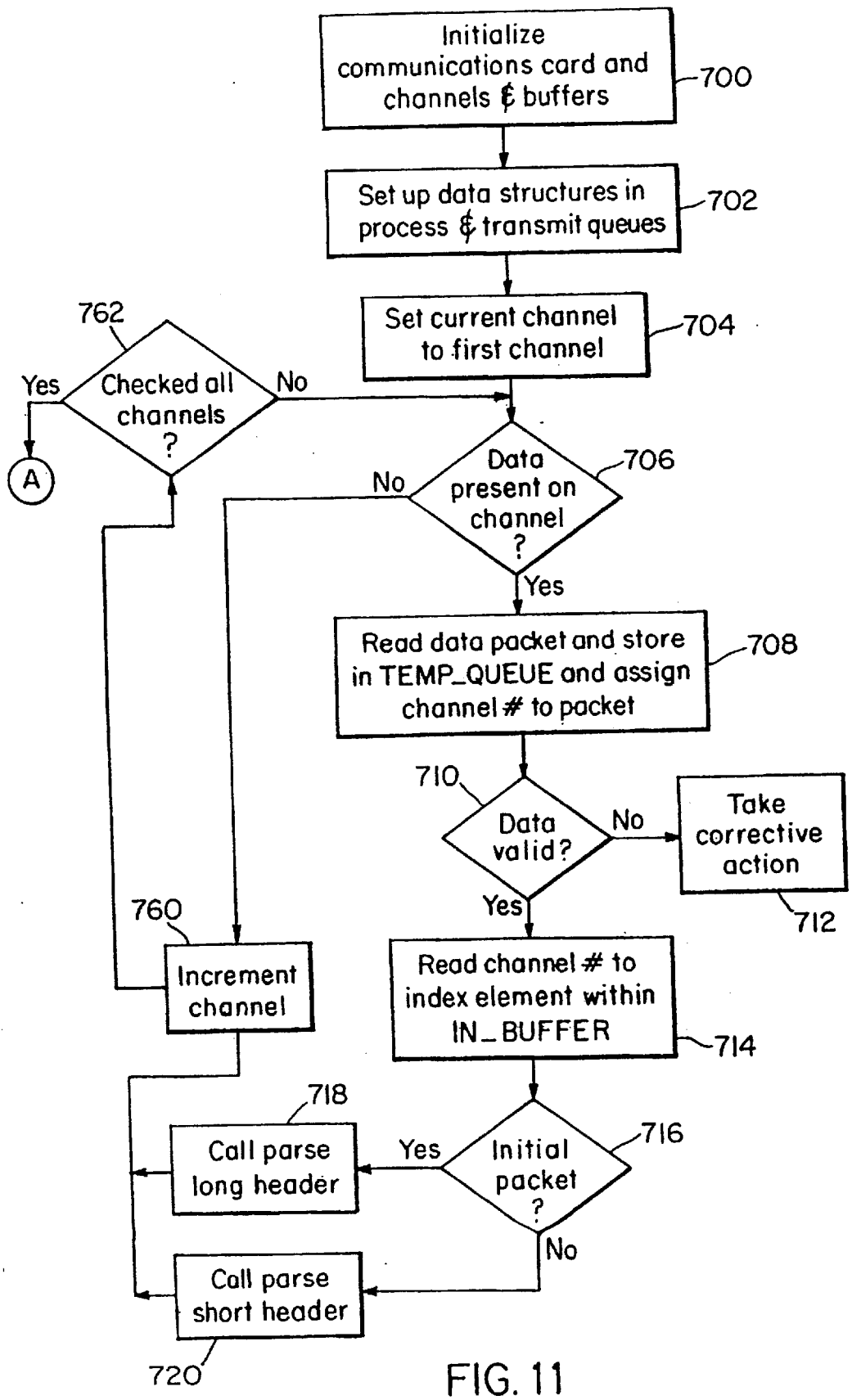
FIG. 11 illustrates the processing sequence by which the communication server reads packets transmitted from the handheld interface.

FIG. 11 illustrates the processing sequence by which the communication server 12 receives messages from the handheld interface 8, processes these messages and transmits these messages to the command server 14. First, the I/O card 102 is initialized, along with the communication channels, buffers and queues (step 700). Next, the data structures for the message list, COM_INFO, CMD, and short and long headers are set up (step 702). A current channel to be read by the I/O card 102 is initialized to the first channel (step 704). Next, the current channel is tested to determine whether data is being transmitted thereon from the corresponding handheld interface 8 (step 706). If data is present, the packet of transmitted data is read and stored in the temporary buffer 104 (step 708). The packet of data is stored within the temporary buffer 104 at the array address corresponding to the current channel. A channel identifying number corresponding to the transmitting handheld interface 8 is also assigned thereto by the I/O card 102.

Next, a check sum field within the data packet is tested to determine whether the transmitted data is valid (step 710). If the data is invalid, the communication server takes the necessary corrective actions (step 712). If the data is valid, the CPU 106 requests the channel number (step 714) and the packet 300 from the I/O card 102 and utilizes the channel number to index the correct corresponding element within the input buffer 108. Next, it is determined whether a packet is an initial frame or a subsequent frame of a message (step 716). To effect this test, the message total field, within the element of the input buffer 108 corresponding to the current channel, is read and compared to zero. If the message total field equals zero, then a packet has not yet been written to this element of the input buffer 108. Thus, the packet being read is identified as an initial packet which will include the long header structure. Otherwise, the packet is identified as one containing the short header structure. In either case, the packet number is incremented within the currently indexed element of the input buffer 108.

If the packet contains the long header structure, processing moves to step 718 in which the parse long header function is invoked. If the packet includes the short header structure, processing moves to step 720 where the parse short header function is invoked.

Figure 12:
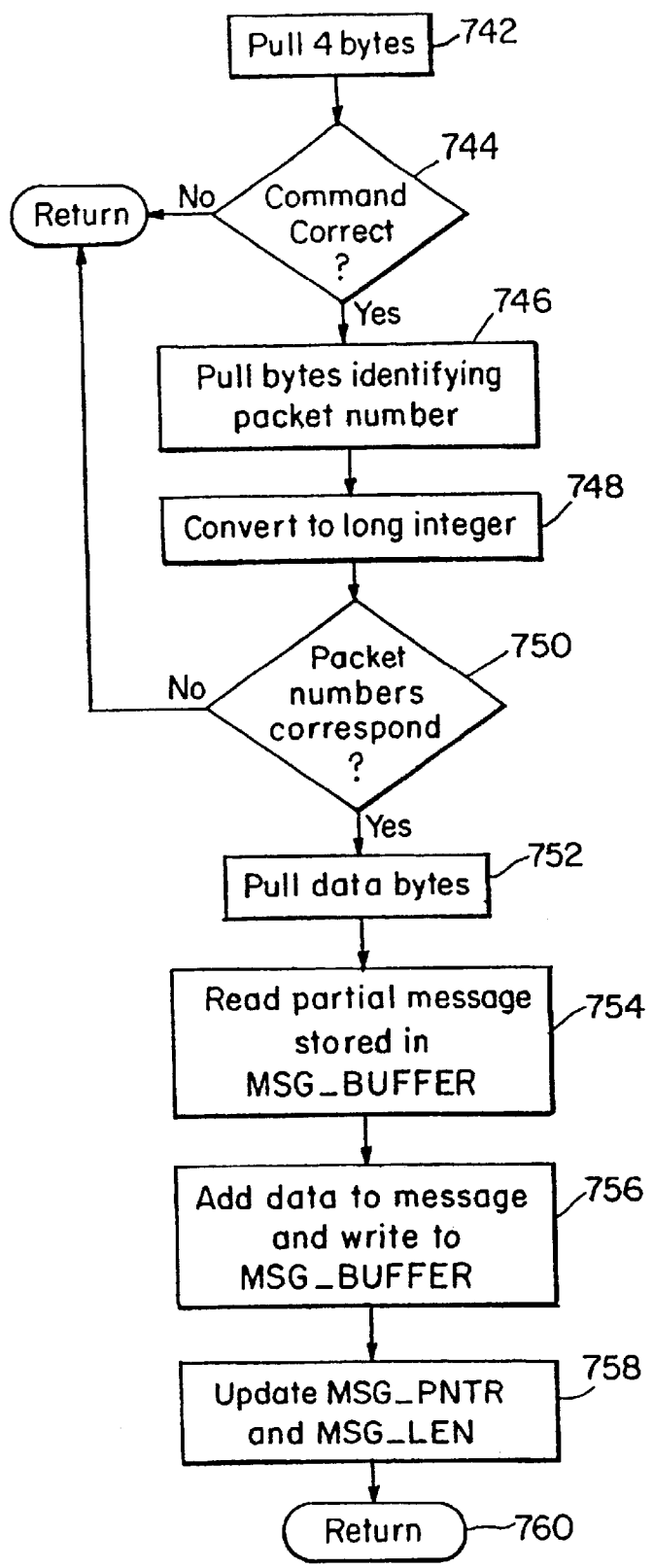
FIG. 12 illustrates the processing sequence by which the communication server parses through a short header structure within an incoming packet to build the input buffer.

FIG. 12 and FIG. 13 illustrate the parse long and short header functions. Within the parse long header function, the first four bytes of the data packet within the temporary queue is read as the command (step 722). This command is compared with a list of valid commands and if the command is invalid the processor takes the necessary corrective action (step 724). If the command is valid, the command is written to the command field within the element of the input buffer 108 indexed by the corresponding channel number (step 726). Next, the subsequent six bytes of the packet within the temp buffer is read as the User ID, if present, of the destination user for the attached message/data. This six byte ID is stored in the UserID_To field of the element within the input buffer 108 indexed by the current channel number (step 728). The User ID, corresponding to the signed on user, is added to the UserID_From field of the indexed element.

Next, the subsequent four bytes are read from the packet within the temporary buffer 104 as the total length of the following message (e.g., the total number of bytes to follow within one or more packets corresponding to the present message) (step 730). The four byte value representing the message total is converted to a long integer (step 732) and assigned to the message total field within the element of the input buffer 108 indexed by the current channel number (step 734). Thereafter, the data section within the packet is written to the message buffer as a data string and the length thereof is stored within the message length field within the presently indexed element of the input buffer 108 (step 736).

A message pointer pointing to the data string within the message buffer 110 is stored within the message pointer field of the indexed element within the input buffer 108 (step 738). Finally, the element of the temporary buffer 110 is cleared (step 740). In this manner, steps 718–740 parse through a packet having a long header structure, create the COM_INFO structure within the input buffer 8 and store the message 302 from the handheld interface 8 within the message buffer 110.

Returning to FIG. 11, if in step 716 it is determined that the packet is not an initial packet, then the short header function is invoked (see FIG. 13). First, the first four bytes of the packet are pulled (step 742) and compared with the value in the command field of the currently indexed element within the input buffer 108 (this command is indexed based on the channel number) to determine if these commands are the same (step 744). If not, the system takes the necessary corrective actions (step 746). If the commands correspond, the packet number within the short header is pulled (step 746), converted to a long integer (step 748) and compared to the packet number (plus one) within the indexed element of the input buffer 108 (step 750). These packet numbers must correspond to ensure that the received packet is the next packet to be added to the input buffer 108. If the packet numbers correspond, the present packet is identified as part of the message corresponding to the presently indexed element within the input buffer 108 and processing flows to step 752, else it returns. If the packet is not matched based on above criteria, then a corrective action is taken.

Next, the data within the temporary buffer 110 is pulled (step 752) and the portion of the message already stored in the message buffer 110 is read (step 754). The new data is added to the end of the stored message and the new total string is rewritten to the message buffer 110 (step 756). The message pointer (MSG_From_HH) and the message length (MSG_LEN) are updated within the corresponding fields of the COM_INFO of the indexed element of the input buffer 108 (step 758). Thereafter, the control returns to the main process (step 760).

Referring to FIG. 11, once control is returned to the main program, the current channel is incremented (step 760). Next, it is determined whether all channels have been checked (step 762). If so, control is set to the processing sequence (at point A). If all of the channels have not been checked, control returns to step 706. This process is continuously performed until all of the channels have been checked thereby transferring all packets of data from the temporary buffer 104 to the input buffer 108 and message buffer 110.

Figure 14:
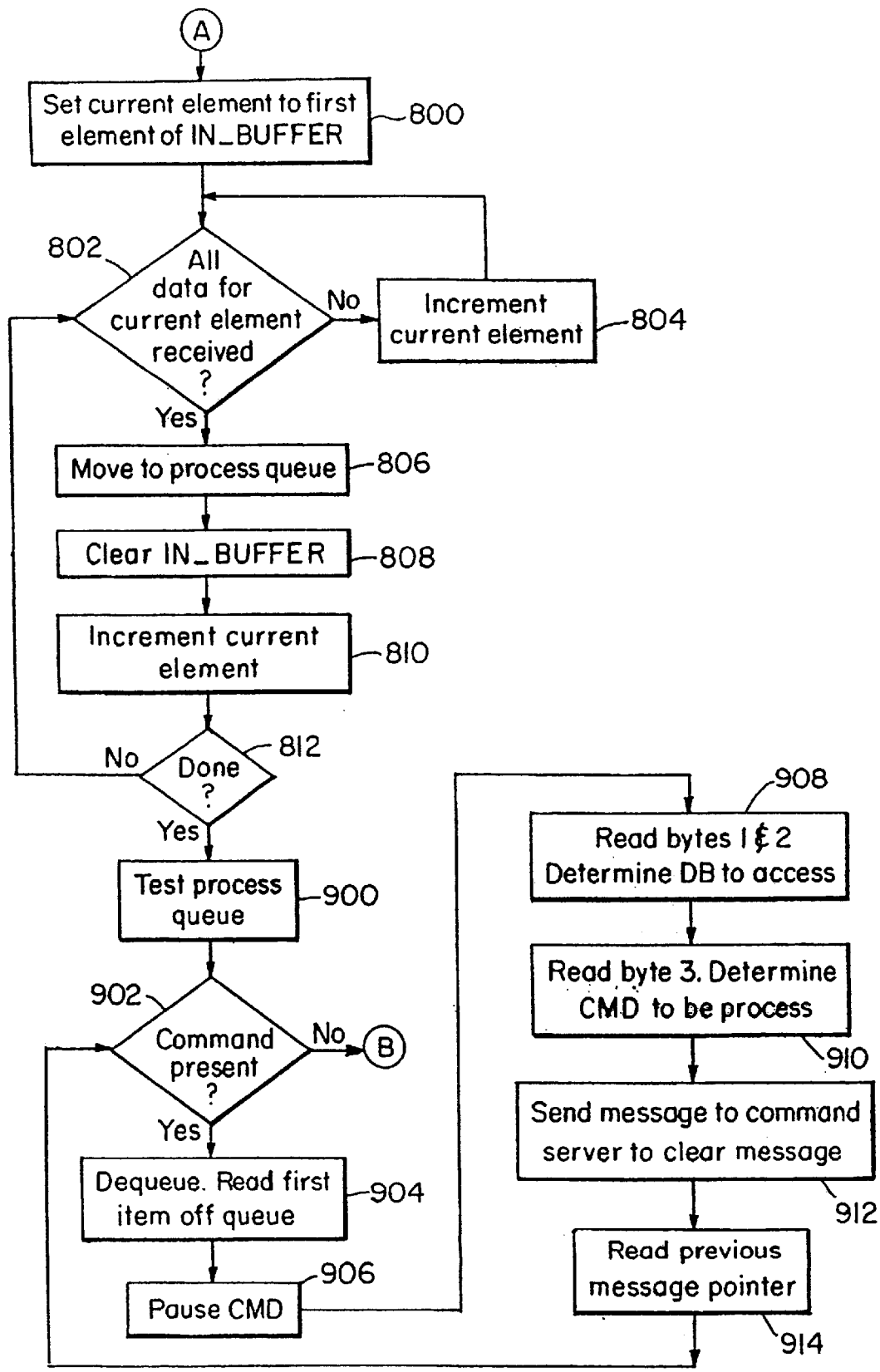
FIG. 14 illustrates the processing QUEUE sequence to move completed messages to the processing QUEUE.

Next, processing moves to the processing queue sequence (FIG. 14) to move completed messages 302 to the processing queue 112. First, the current element pointer into the input buffer 108 is set to the first input buffer element (step 800). Then, it compares the message total length (MSG_Total) with the message length (MSG_LEN) to determine whether a complete message corresponding to the current element within the input buffer 108 has been received and stored in the message buffer (step 802). If not, the incomplete message remains on the input buffer 108 and the current element pointer is incremented (step 804) and the process returns to step 802.

If the complete message for the current element has been received, the message is placed on the processing queue (step 806) by creating a message list therefor. To do so, the command information (COM_INFO) of the current element of the input buffer 108 is written to the processing queue 112 and stored in the command information (COM_INFO) section therefor. As the corresponding message represents a transmission from the handheld interface 8 to the command server 14, the next four fields of the indexed message list element in the processing queue remain undefined. This message list is "pushed onto the back" of the processing queue by storing, in the preceding message list in the processing queue, a pointer to the current message list. This pointer is stored in the final field (Previous_MSG_LST) within the previous, most recent message list added to the processing queue (step 806).

Once the command information has been moved to the processing queue, the corresponding element of the input buffer 108 is cleared (step 808). Thereafter, the current element pointer into the input buffer 108 is incremented (step 810) and it is determined whether or not every element of the input buffer 108 has been tested (step 812). If not, processing returns to step 802 and the next element within the input buffer 108 is processed. If processing is done on the input buffer 108, control moves to process the message lists on the processing queue.

The first element of the processing queue is tested to determine whether a command is stored therein (steps 900 and 902). If a command exists on the processing queue, this command is "dequeued" (step 904) by reading the message information from the processing queue (which is stored in the message list structure). The command field (CMD) within the COM_INFO section of the message list is read. The message is parsed into specific components (step 906), by reading the first two bytes of the command field, converting these bytes to a long integer form and storing the data base identifier in the Data_File field of the message list (step 908). Next, the third byte of the command (CMD) field in the COM_INFO structure is read and stored in the Command field of the message list (step 910). Then the actual data message is appended to the message list structure based on the message pointer (MSG_TO_HH) and the message length (MSG_LEN) are reset (step 912). The communications server 12 sends the message to the appropriate command server 14 based upon the database and command code (step 912).

Next, the previous message pointer (Previous_MSG_LST) is read from the current message list to determine the next message to be processed on the queue (step 914) and control is returned to step 902. In this manner, each message upon the processing queue 112 is parsed through and transmitted to the appropriate command server 14. When no more commands are on the processing queue, control is moved to the create transmit queue module (step 916) (FIG. 15).

Figure 17:
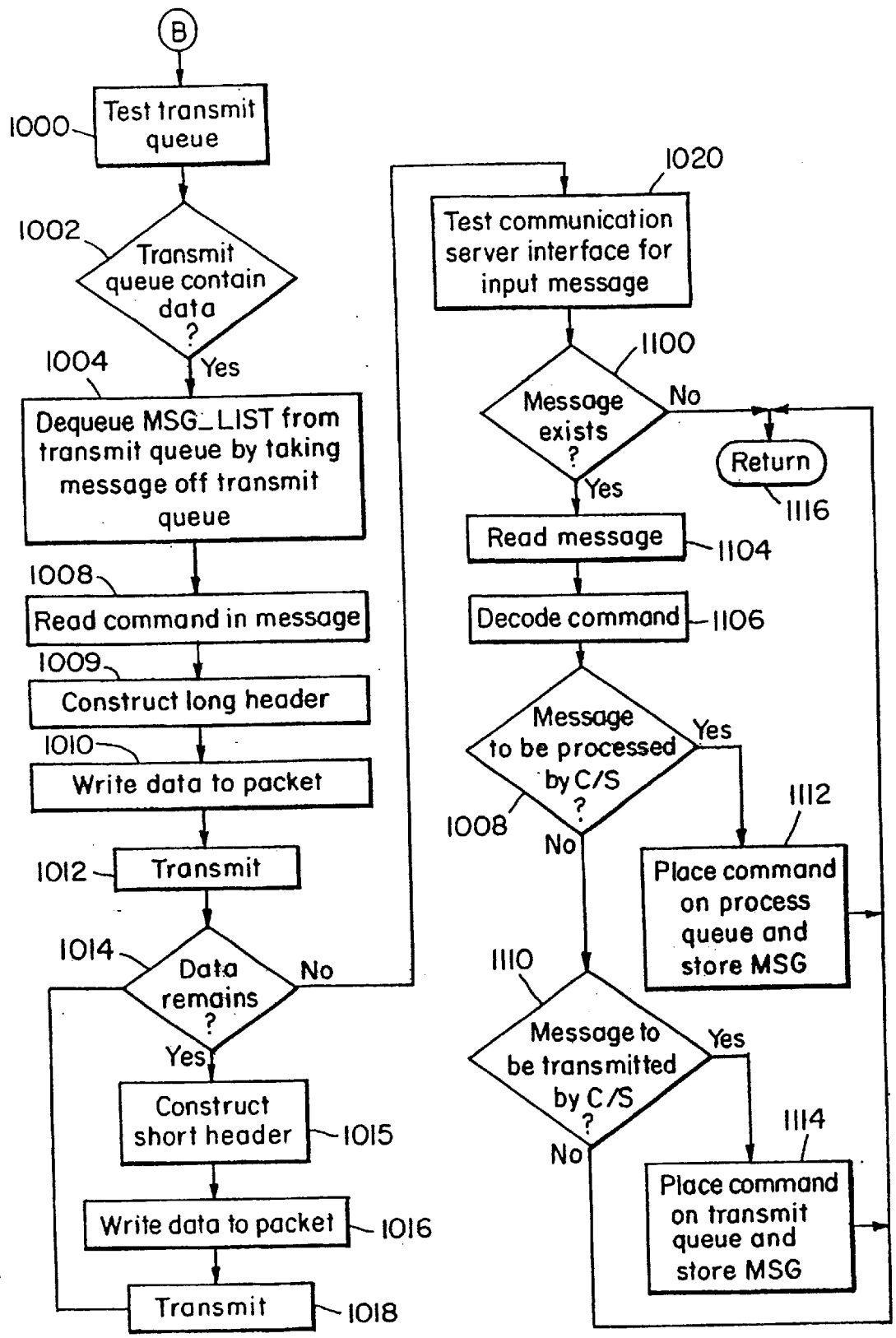
FIG. 17 illustrates a block diagram of the communications server.

FIG. 17 illustrates the process by which the communication server 12 processes messages upon the transmit queue which are to be sent to the handheld interface 8. First, the first message upon the transmit queue is tested (step 1000) to determine whether data is contained therein (step 1002). If data exists, the message is dequeued by taking the message off the transmit queue (step 1004). Next, the command information from the message list is read and a long header constructed for the first packet to be transmitted to the handheld interface 8 for the message (steps 1008 and 1009). Next, the data from the message is written to the packet and transmitted (step 1010 and 1012). Thereafter, it is determined whether additional data remains to be transmitted to the handheld interface 8 (step 1014). If yes, a short header is constructed (step 1015) and additional data from the message is written to the packet containing the short header (step 1016).

Once constructed, the packet containing the short header is transmitted (step 1018) and processing returns to step 1012 at which it is determined if more data remains. This loop is repeated until the entire message has been transformed from the message list structure into data packets and transmitted to the handheld interface 8. Once the entire message has been transmitted, control passes to the next module (step 1020).

The communications server 12 tests the communication bus 6 and determines if messages have been sent from other communication servers. First, the communications bus is tested to see if a message exists (step 1100). If a message exists, the message is read (step 1104) and the command therefor is decoded (step 1106). Thereafter, the command is tested to determine whether the message should be transmitted to a corresponding handheld interface 8 or whether the message should be transmitted to a command server connected to the communication server 12 (steps 1108 and 1110). Thereafter, the message is placed on the transmit or processing queue depending upon the destination of the message (steps 1112 and 1114). Thereafter, control is returned to the main program (step 1116). This process is continuously repeated until the communication server 12 is turned off. Once turned off, the communications channels are closed and the system is turned off.

Command Server

The command server operates to update the corresponding databases based upon messages received from the communications server. The command server utilizes a conventional software package for managing these databases, such as Pro-tree (version 2.0). Other database managing systems may be used to access the data base, such as DBase, CodeBase, B-Trieve, Cisam and the like. Particular commands within the conventional management system are called depending upon the command code and database codes transmitted within the message list.

Figure 19:
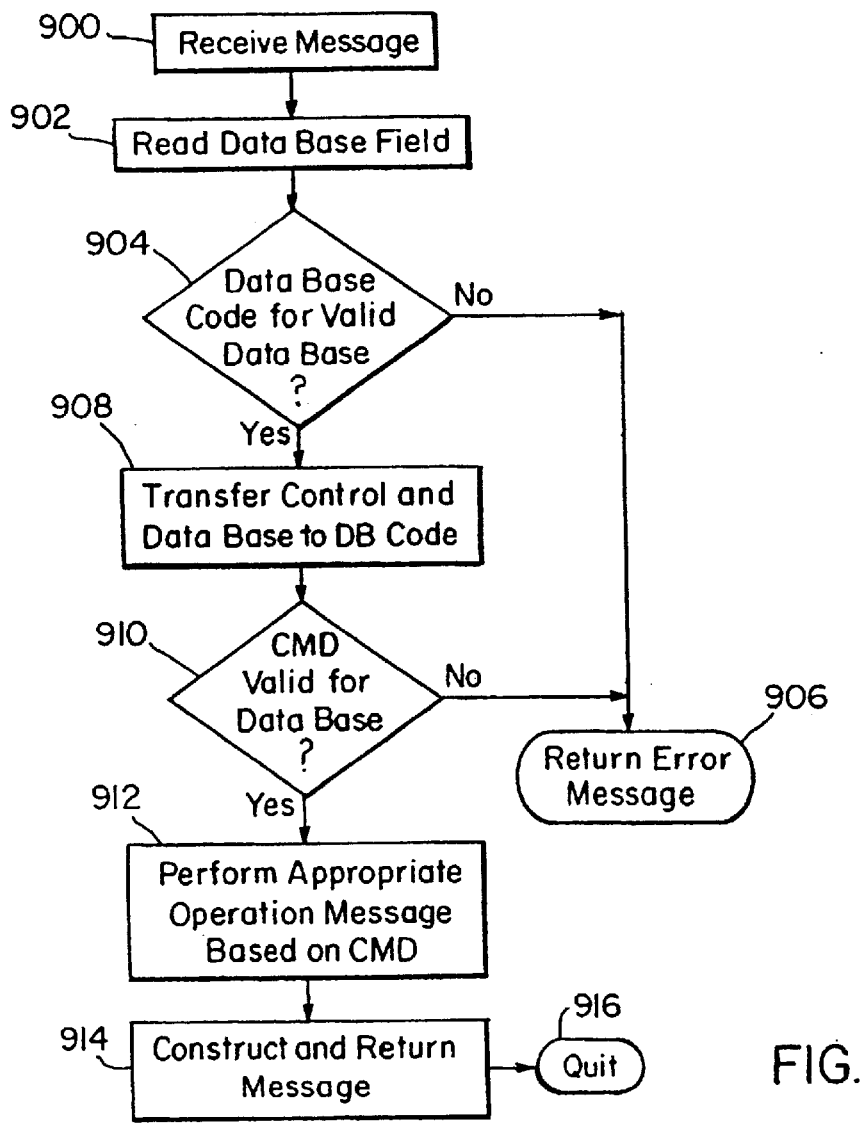
FIG. 19 illustrates the processing sequence of the command server to process and transmit message lists.

FIG. 19 illustrates the process by which the command server 14 invokes the database management functions. First, the command server 14 receives a message (step 900), including the complete message list structure followed by the data message. Next, the command server 14 reads the data base file field (step 902) and determines whether that data base code is valid for the present command server 14 (step 904). If not, it returns an error message (step 906). If so, control is transferred to the database routine corresponding to the command code (CMD) in the Command field of the message list (step 908). Next, it is determined whether the command code is correct for the addressed database (step 910). If not, it returns an error code (step 906). If so, it accesses the message data within the message list and performs the appropriate operation upon the data base (step 912). Thereafter, it constructs a return message using the data returned from the database into the structure of the message list (step 914) and quits (step 916).

To invoke the database managing functions, the command number is processed within a case statement, whereby each case within the case statement corresponds to a unique command number. Each case statement calls the appropriate routines. For instance, command number 7 may represent an add command, and thus, case "7" would direct the command server to read the data from the message and write this data to the next address within the database. Similarly, the command number within the message may represent a read or request operation, in response to which, the corresponding case would direct the command server to read the desired information from the database corresponding to the user ID transmitted within the message. The command server thereafter adds this data to the message and retransmits it to the communications server.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings 1–19 is to be interpreted as illustrative, and not in a limiting sense.

The following appendix sets forth descriptions of the modules and functions used by the present system.

Glossary key—an area of the screen that has been registered with the opening system as an area where an event is expected. If an event does not occur within this area, an integer identifier will be returned by the operating system indicating that the event did occur.

event—the screen was touched, if it was touched in an area defined by a key, then return the identifier.

scrolling text window—a key where scrolling text will reside.

scroller—a key associated with the scrolling text window, the scroller has a bar in it to indicate where the text within the text window is in relationship to the rest of the text.

scrollbar—the tool used for entering vitals (darkened from the very bottom of the key to the value chosen by the user).

rolling key—a key with a digit in it, when the key is touched, that digit is incremented. If the digits value is 9 and it is incremented, it will contain the value 0 with no carry performed.

Module scrollbar.c—contains all functions for the scroll bar functions to be used by other modules.

init_scroll_bar—initializes all necessary variables and draws all of the detail.

get_scroll_bar_value—upon an event in the scroll bar key, this routine is called and it handles that event, then it returns the value that the scroll_bar is pointing to (the value point pointed to by the user).

set_scroll_bar_value—the user can set the value anytime.

functions to be used internally by this module draw scroll_bar—draws the inside of the scroll_bar.

Module vital_input—contains all the functions used to perform the vital input note—the Mode value indicates what is being input at the moment, if the user has chosen systolic, then the systolic rolling keys are inverted and activated, and the scroll bar will have the systolic data in it.

possible modes—systolic, diastolic, pulse, temperature, respiratory.

Write_Keys_Data—this routine redraws the rolling keys associated with a certain mode, (example, if the mode is pulse and the user somehow changes the value, this routine draws the 100s value in the leftmost key, the 10s value in the middle key, and the 1s value in the rightmost key):

ChangeMode—changes the mode of the screen, this involves (1) turning off the old mode (example—pulse); (2) turning on the rolling keys of the new mode (example—systolic) so now an event may occur—also invert the keys so that they are white on black; and (3) calling Init_scroll_bar to redraw the scroll bar with the new modes details.

EnterVitalsDraw—draw the detail on the entire screen (1) write patients name (2) write last date and time that the vitals were entered (3) write the last vitals values (4) turn off all rolling keys (5) change the mode to systolic by calling changemode inc_value—increment the values in the rolling keys, then call Write-Keys_data. inc_temp—same as inc_value, but allow the 100's key to contain the values 0, 1, 2, 3, 4, 5, 6, 7, 8, 9, 10, 11.

Do_vital_input—THE MAIN ROUTINE (1) calls EnterVitalDraw (2) contains the case statement that handles events.

Module graph.c—draws the graph on the screen.

make_graph—receives x, y values, x axis label, y axis label, the type of data that the x and y values are (time, short int, int, long int, float, etc.) and draws the graph, depending upon the type of data in x and y, it calls a simple routine that turns the x, y values into x, y plotting points on the screen.

Module patinput.c—contains all of the functions used to pick a patient.

DoPatientInput—does the entire screens functionality within this one routine.

1—init_scroller—passes in the patient list and the two keys (scroller key and scrolling text key).

2—handles all events.

events in the case that the user picks A–Z, that letter is concatenated onto the search string which is initially empty, then a sequential search upon the text strings is performed to find the first text which is greater in alphabetical value than the search string, then that value is chosen via the function set_scroller_value.

in the event the user touches the scroller then get_scroller_value is called.

in the event the user touches the scrolling text key, then get_scroll_text value is called.

Module vital_1.c—the starting point of the program contains all function calls.

note—Every single "screen" that is called from any other "screen" will be associated by a Calling Identifier (Call ID).

DoMainMenu—two main case statement case statement #1 handles the events of the main menu, if an event occurs in any of the keys of the main menu, then store the CallID in the variable called ReturnCode.

case statement #2 while ReturnCode is not equal to 0 loop the case statement.

since the ReturnCode is not 0, call the appropriate function associated with the Calling Identifier stored in the variable, the function called will eventually return a code that will again be stored in the variable RetCode.

Module scroller.c—contains all functions for the scrolling text windows.

functions to be used by other modules init_scroller—initializes all necessary variables and draws of all the detail.

get_scroller_value—upon an event in the scroller key, this routine is called and it handles that event, then it returns the value that the scroller is pointing to (in our program, this value is the index into an array of strings—points to the text that was picked).

set-scroller_value—the user can set the value any time get_scroll_text_value—upon an event in the scroll text window, this routine is called and it handles that event, then it returns the same value as does the get_scroller_value function.

functions to be used internally by this module draw_scroller—draws the bar inside of the scroller, then calls draw_scroll_text.

draw_scroll-text—draws all of the text that appears in the scrolling text window.

invert_picked_text—inverts the text that is being pointed to by the user.

Major Functions open_ir—used to initial the IR communication with the AndroDat Card and setup the communication channels with each device.

close_ir—used to close all communication channels with the hand held.

init_com_info—used to reset and clear all data contained for one specified com)info buffer. This routine is called initially to initialize each buffer and ready to receive data. After a message has been received and put on the process queue, this routine is used to clear the old data and ready the input buffer for the next command.

collect_messages—this routine will read through each input channel to see if a message exists. If one exists, then the message will be read into a temporary buffer and passed to the routine place_message for placement on the input buffer.

place_message—this routine will determine if the message being read is the first or subsequent message. If the message is the first packet, then the routine parse_long_hdr is called. If the packet is the second or subsequent message, the routine parse short_hdr is called.

parse_short_hdr—this routine is used to parse the structure tmp_buffer, validate the command being sent along with the correct packet number, then place the data in the appropriate in_buffer message structure. This routine is called after the initial command packet is sent.

parse_long_hdr—this routine is used to parse the structure tmp-buffer, validate the command being sent. This routine then initializes the in_buffer structure and finally places the data in the in buffer messages structure. This routine is called when a handheld device sends its initial packet for requesting a command.

comm_server—this routine is the main routine which controls the logic flow of the entry communication server system.

process_in_buffer—this routine is used to search the in-buffer for completed messages to be placed on the process queue. This routine determines if a message is finished if msg_total=-msg_len and msg_total>0. This routine calls ENQUEUE to physically put the message on the process queue.

process_cmd—this routine is used to take the next message off the command queue then send it to the correct server for processing. This routine calls the dequeue function to physically dequeue the item off the command queue.

process_transmit—this routine is used to take the next message off the transmit queue then send it to the correct server for processing. This routine calls the dequeue function to physically dequeue the item off the transmit queue.

packet_msg—this routine is used to physically send the message from the communication server to the handheld computer via the AndroDat Card. It is responsible for all packets of the data and verify of successful transmission.

enqueue—this routine takes completed messages and places them on the queue. A parameter is passed to which queue to place the message along with the data to queue.

dequeue—this routine will take messages off the queue and place them in a temporary buffer to be processed by the communication server. A parameter is passed to which queue to process along with the temporary space to put message.

nulqueue—this routine is used to initialize a queue and prepare it to start receiving data. Call to this routine will destroy any data existing in the queue.

com_info—this structure is used to store the incoming message from the handheld in_buffer—this is an array of the structure com_info. This structure is used to hold the individual messages being received from the handheld computers.

message_list—this structure is used to serve as the queuing functions for the command processing and data transmission.

long_hdr—this is the structure of the header for initial communication to the server.

short_hdr—this is the structure for second and subsequent communications of the second command.

What is claimed is:

1. A bar-code-driven data acquisition and management system comprising:
at least two input computers, operably coupled via a communication link, each said input computer being coupled to a respective local database of data records; and
at least two portable computing devices, each said portable computing device being operably coupled to one of the two input computers via a wireless communication channel for accessing and updating the data records in the local databases of the at least two input computers, wherein each portable computing device comprises:
a CPU for controlling operation of the portable computing device;
memory storing at least one data set, each data set having multiple data fields storing data values;
a touch sensitive display device for displaying at least a data I/O screen and for sensing contact by a user, the CPU defining multiple virtual regions upon the data I/O screen, each virtual region corresponding to a data field, the touch sensitive display device sensing contact by the user within a virtual region, the touch sensitive display device displaying within each virtual region a data value for the associated data field from a current data set, and the CPU identifying a virtual region contacted by the user and effecting an interface control associated therewith; and
an optical scanning device for reading bar codes encoding data values for data fields corresponding to at least one virtual region displayed upon the data I/O screen and displaying such data values thereupon.

2. The bar-code-driven data acquisition and management system of claim 1, wherein the CPU of each portable computing device executes a graphical user interface that includes an event handler, the event handler:
identifying one of the virtual regions that corresponds to the location of user contact,
determining a specific event identifier corresponding to the identified virtual region, and
processing a predetermined sequence for the specific event identifier.

3. The bar-code-driven data acquisition and management system of claim 2, wherein each virtual region of the graphical user interface corresponds to a predefined processing sequence which is initiated by the user by contacting the associated virtual region.

4. The bar-code-driven data acquisition and management system of claim 3, wherein the predefined processing sequence involves one of a data entry operation, a data transmit operation for communicating data stored thereto to another computing device, and a code scan operation for data entry.

5. The bar-code-driven data acquisition and management system of claim 2, wherein the graphical user interface further comprises a virtual keypad displayed on the data I/O screen for entering symbols associated with keys of the keypad.

6. The bar-code-driven data acquisition and management system of claim 2, wherein the graphical user interface further comprises at least one scroll bar displayed on the data I/O screen.

7. The bar-code-driven data acquisition and management system of claim 2, wherein the graphical user interface further comprises at least one scroll bar format and a rolling key format.

8. The bar-code-driven data acquisition and management system of claim 2, wherein the graphical user interface further comprises a menu screen and a graphing screen, wherein each selection from the menu screen corresponds to a virtual region and an associated processing sequence.

9. The bar-code-driven data acquisition and management system of claim 2, wherein the graphical user interface displays multiple icons.

10. The bar-code-driven data acquisition and management system of claim 2, wherein the graphical user interface comprises a text input mechanism that enables the user to enter at least a portion of a desired text data, that automatically searches data stored in memory to retrieve text data closest to the portion of desired text data entered, and displays the retrieved text data on the data I/O screen.

11. The bar-code-driven data acquisition and management system of claim 1, wherein each input computer comprises:
   a first server that manages the local database coupled thereto; and
   a second server for receiving and transmitting packets of information to and from at least one portable computing device over the respective wireless communication channels.

12. The bar-code-driven data acquisition and management system of claim 11, wherein the at least two input computers are part of a computing tier comprising:
   a plurality of first servers for managing local databases coupled thereto;
   a plurality of second servers for receiving and transmitting packets of information to and from the portable computing devices, wherein a given second server selectively communicates with the portable computing devices located within a predefined region proximate thereto; and
   wherein the plurality of first servers and the plurality of second servers communicate one another via a communications network.

13. The bar-code-driven data acquisition and management system of claim 12,
   wherein a given second server is associated with one of the plurality of first servers;
   wherein the given second server interacts with a given portable computing device located with a predefined region proximate thereto to service requests communicated from the given portable computer; and
   wherein, upon determining that one of said requests requires access to data stored in a local database associated with a first server other than the one first server, the one request is communicated over the communications network to the other first server to access said data stored in the local database coupled thereto, and said data is returned to the given second server over the communications network for communication to the given portable computing device.

14. The bar-code-driven data acquisition and management system of claim 12, wherein the plurality of second servers and the communications network therebetween enables communication of data between the portable computing devices.

15. The bar-code-driven data acquisition and management system of claim 12, wherein communication between a given second server and each portable computing device is selected based on the predefined region and position of the portable computing device.

16. The bar-code-driven data acquisition and management system of claim 1, wherein the data values encoded by the bar codes represent information related a medical patient.

17. The bar-code-driven data acquisition and management system of claim 16, wherein the data values encoded by the bar codes represent one of personal information gathered upon admittance for care, information related to past medical history of the medical patient, and information related to vital statistics of the medical patient.

18. The bar-code-driven data acquisition and management system of claim 17, wherein the vital statistics include one of systolic, diastolic, pulse, temperature and respiratory information.

19. The bar-code-driven data acquisition and management system of claim 1, wherein each portable computing device comprises a message notification mechanism that notifies the user of receipt of a message from one of the input computers over the respective wireless communication channels.

20. The bar-code-driven data acquisition and management system of claim 19, wherein the message notification mechanism generates one of an audio signal, a video signal and vibration signal.

21. The bar-code-driven data acquisition and management system of claim 1, wherein communication of data between the at least two portable computing devices occur over the respective wireless communication channels and the communication link operably coupling the two input computers.

22. The bar-code-driven data acquisition and management system of claim 1, wherein the data values encoded by the bar codes represent product information.

23. The bar-code-driven data acquisition and management system of claim 1, wherein the data values encoded by the bar codes represent information identifying a medical patient.

24. The bar-code-driven data acquisition and management system of claim 2, wherein each portable computing device comprises local memory storing information loaded from the data records of at least one of the local databases via the respective wireless communication channels.

25. The bar-code-driven data acquisition and management system of claim 1, wherein each portable computing device comprises a graphical user interface for interacting with a user to enter user-supplied information, wherein the user-supplied information is communicated to at least one of the input computers over the respective wireless communication channels for storage in the local database coupled thereto.

* * * * *